United States Patent [19]
Cohen et al.

[11] Patent Number: 5,780,034
[45] Date of Patent: Jul. 14, 1998

[54] DIAGNOSIS AND TREATMENT OF INSULIN DEPENDENT DIABETES MELLITUS USING HEAT SHOCK PROTEIN DETERMINENTS

[75] Inventors: Irun R. Cohen; Dana Elias; Doron Markovits, all of Rehovot, Israel

[73] Assignee: Yeda Research and Development Co. Ltd., Rehovot, Israel

[21] Appl. No.: 384,454

[22] Filed: Feb. 3, 1995

Related U.S. Application Data

[63] Continuation of Ser. No. 937,449, Aug. 31, 1992, abandoned, which is a continuation of Ser. No. 493,127, Mar. 14, 1990, abandoned, which is a continuation-in-part of Ser. No. 371,249, Jun. 26, 1989, Pat. No. 5,114,844, which is a continuation-in-part of Ser. No. 322,864, Mar. 14, 1989, abandoned.

[51] Int. Cl.$^6$ .......................... A61K 38/00; A61K 39/04
[52] U.S. Cl. .................... 424/185.1; 424/248.1; 424/278.1; 530/350; 530/395; 530/868
[58] Field of Search .................. 424/184.1, 185.1, 424/248.1, 279.1; 530/350, 395, 868

[56] References Cited

U.S. PATENT DOCUMENTS 5,114,844  5/1992  Cohen ........................... 435/7.21

FOREIGN PATENT DOCUMENTS

| | | |
|---|---|---|
| 0261648 | of 1987 | European Pat. Off. |
| 0262710 | of 1987 | European Pat. Off. |
| 0262710 | 4/1988 | European Pat. Off. |
| 0333606 | of 1989 | European Pat. Off. |
| 8505034 | 11/1985 | WIPO |

OTHER PUBLICATIONS

Cohen, Irun R., ":The Self, The World and Autoimmunity", *Scientific American*, vol. 256, pp. 52–60 (1988).
Thole et al. "Characterization, Sequence Determination, and Immunogenicity of a 64–Kilodalton Protein of Mycobacterium Bovis BCG Expressed in *Escherichia col* K–12", *Infection and Immunity*, vol. 55, No. 19, pp. 1466–1475, (1987).
Baekesov et al, "Autoantibodies in Newly Diagnosed Diabetic Children Immunoprecipitate human Pancreatic Islet Cell Proteins", *Nature*, vol. 298, pp. 167–169 (1982).
Minolta et al, "Autoantibodies to the Heat–Shock Protein hsp90 in System Lupus Erythematosus", *J. Clin. Invest.*, vol. 81, pp. 106–109 (1988).
Res et al, "Synovial Fluid T Cell Reactivity Against 65 kD Heat Shock of Mycobacteria in Early Chronic Arthritis", *The Lancet*, vol. II, pp. 478–480 (1988).
Vandenbark et al, "Immunization with a Synthetic T–Cell Receptor V–Region Peptide Protects Against Experimental Autoimmune Encephalomyelitis", *Nature*, vol. 341, pp. 541–544 (1989).
Howell et al, "Vaccination Against Experimental Allergic Encephalomyelitis with T Cell Receptor Peptides", *Science*, vol. 246, pp. 668–670 (1989).
S. Jindal et al. May 1989 Mol. Cell. Biol. 9(5):2279–2283. "Primary Structure of . . . ".

D. Elias et al. Feb. 1990. PNAS 87:1576–80. "Induction and Therapy of Autoimmune Diabetes. . . ".
Atkinson, M. A. et al. Scientific American, Jul 1990. pp. 62–71. "What Causes Diabetes?".
Paul, W.F. (ed). Immunology. 1989 pp. 580–583.
Baekkesov, S. et al., "Identification of the 64K Autoantigen in Insulin–Dependent Diabetes as the Gab–Synthesizing Enzyme Glutamic–Acid Decarboxylase", *Nature*, v. 347, No. 6289 (1990), pp. 151–156.
Borek, F., "Immugenicity", ed, North–Holland Publishing Co., Amsterdam, 1972; Chapters 3 and 4.
Dorian's Illustrated Medical Dictionary, 27th Edition, W.B. Saunders Co., pub., 1988, p. 1354.
Robbins, S.L. et al. *Pathological Basis of Disease*. 4th Edition, 1989, pp. 992–999.
Yang, X–D. et al. Experientia, vol. 48, pp. 650–656, 1992. Heat Shock Proteins in Autoimmune Disease.
Dubas, P. Res. Immunol. 140:653–9. 1989. "Heatshock Proteins and Immunity."
F. Emmrich et al., "A Recombinant 64 Kilodalton Protein of Mycobacterium Bovis Bacillus Calmette–Guerin Specifically Stimulates Human T4 Clones Reactive to Mycobacterial Antigens," *J. Exp. Med.*, vol. 163(4) pp. 1024–1029, Apr. 1986.
T. Ottenhoff et al., "Evidence for an HLA–DR4–Associated Immune–Response Gene for Mycobacterium Tuberculosis" *The Lancet*, vol. 3, No. 8502, pp. 310–313, Aug. 9, 1986.
R. Young et al., "Dissection of Mycobacterium tuberculosis antigens using recombinant DNA," *Proc. Natl. Acad. Sci., USA*, vol. 82, pp. 2583–2587, May 1985.
J. Thole et al., "Cloning of *Mycobacterium bovis* BCG DNA and Expression of Antigens in *Escherichia coli*," *Infection and Immunity*, vol. 50, No. 3, pp. 800–806, Dec. 1985.
T. Shinnick et al., "The Etiologic Agents of Leprosy and Tuberculosis Share an Immunoreactive Protein Antigen with the Vaccine Strain Mycobacterium bovis BCG," *Infection and Immunity*, vol. 55, No. 8, pp. 1932–1935, Aug. 1987.
*Proc. Natl. Acad. Sci. –USA*; vol. 88, No. 8, 1991, Washington, DC, USA. pp. 3088–3091; D. Elias et al: "Vaccination against autoimmune mouse diabetes with t–cell epitope of the human 65–kda heat shock protein".
*Lancet* vol. 336, No. 2, 8 Sep. 1990, London, UK, pp. 583–585; D.B. Jones et al: "Heat–shock protein 65 as a beta cell antigen of insulin–dependent diabetes".

*Primary Examiner*—Thomas M. Cunningham
*Attorney, Agent, or Firm*—Browdy and Neimark

[57] ABSTRACT

A 65 KD heat shock protein, proteins cross-reactive therewith, antibodies thereto or T cells specific thereto can be used for detecting in humans the existence of, a tendency to develop, or the initiation of a process leading to insulin dependent diabetes mellitus. Antibodies to hsp65 can be used to detect the hsp65 molecule in blood or urine. The hsp65 molecule of any species, or any other substance immunologically cross-reactive therewith, when administered with a tolerogenic carrier, can be used for the prevention or treatment of IDDM prior to development of clinical symptoms thereof. T cells, active fragments thereof or the receptor peptide thereof can also be used for prevention or treatment of IDDM.

18 Claims, 6 Drawing Sheets

FIG. 3A

```
-45   GACGACCCTGTCTCGCCGAGCGCACGCTTGCCGCCGCCCCGCAGAAATGCTTCGGTTACCCACAGTCTTTGCCCAGATGAGACCGGTGTCC
      D  D  L  S  R  R  A  H  A  C  R  R  P  A  E  MetLeuArgLeuProThrValPheArgGlnMetArgProValSer  15

46    AGGGTACTGGCTCCTCCATCTCACTCGGGCTTATGCGAAAGATGTAAAATTTGGTGCAGATGCCGAGCCTTAATGCTTCAAGGTGTAGAC
      ArgValLeuAlaProHisLeuThrArgAlaLeuTyrAlaLysAspValLysPagGlyAlaAspAlaArgAlaLeuMetLeuGlnGlyValAsp  45

136   CTTTTAGCCGATGCTGTGGCCGTTACAATGGGCCAAAGGGAAGAACAGTGATTATTGAGCAGAGTTGGGGAAGTCCCAAAGTAACAAAA
      LeuLeuAlaAspAlaValAlaValThrMetGlyProLysGlyArgThrValIleIleGluGlnSerTrpGlySerProLysValThrLys  75

226   GATGGTGTGACTGTTGCAAAGTCAATTGACTTAAAAGATAAATACAAGAACATTGGAGCTAAACTTGTTCAAGATGTTGCCAATAACACA
      AspGlyValThrValAlaLysSerIleAspLeuLysAspLysTyrLysAsnIleGlyAlaLysLeuValGlnAspValAlaAsnAsnThr  105

316   AATGAAGGAGCTGGGGATGGCACTACCACTGCTCTATAGCCAAGGAAGGCTTCGAGAAGATTAGACAAAGGTGCT
      AsnGluGlyAlaGlyAspGlyThrThrThrAlaThrValLeuAlaArgSerIleAlaLysGluGlyPheGluLysIleSerLysGlyAla  135

406   AATCCAGTGGAAATCAGGAGGAGTGTGATGTTAGCTGTTGATGCTGTAATTGCTGAAACTAAAAAGCAGTCTAAACCTGTGACCACCCCT
      AsnProValGluIleArgArgSerValMetLeuAlaValAspAlaValIleAlaGluLeuLysLysGlnSerLysProValThrThrPro  165

496   GAAGAAATTGCACAGGTTGCTACGATTTCTGCAAACGGAGACAAAGAAATTGGCAATATCATCTCTGATGCAATGAAAAAAGTTGGAAGA
      GluGluIleAlaGlnValAlaThrIleSerAlaAsnGlyAspLysGluIleGlyAsnIleIleSerAspAlaMetLysLysValGlyArg  195

586   AAGGGTGTCATCACAGTAAAGGATGGAAAAACACTGAATGATGAAAATTATTGAAGGCATGAAGTTTGATCGAGGCTATATTTCT
      LysGlyValIleThrValLysAspGlyLysThrLeuAsnAspGluLeuLeuLysThrValAspGluGlyMetLysPheAspArgGlyTyrIleSer  225

676   CCATACTTTATTAATACATCAAAAGGTCAGAAATGTCAGAATTCCAGGATGCCTATGTTCTGTTGAGTCCTGAAGAAAATTTCTAGTATCCAG
      ProTyrPheIleAsnThrSerLysGlyGlnLysCysGluPheGlnAspAlaTyrValLeuLeuSerGluGluLysLysIleSerSerIleGln  255

766   TCCATTGTACCTGCTCTTGAAATTGCCAATGCTCAGCTGAAGGCTTTGGTCATAATCGCTGAAGATGTTGAGAGATGTCTAAGTACA
      SerIleValProAlaLeuGluIleAlaAsnLeuAlaAsnArgLeuAsnArgLeuLysValGlyLeuValLeuLysValAlaLysAlaProGlyPhe  285

856   CTCGTCTTGAATAGGCTAAAGGTTGGTCTTCAGGTTGTGGCAGTCCAAGGCTCCAGGGTTTGGTGACAATAGAAAGAACCAGCTTAAAGAT
      LeuValLeuAsnArgLeuLysValGlyLeuValLeuAlaValAlaLysAlaProGlyPheGlyAspAsnArgLysAsnGlnLeuLysAsp  315
```

FIG. 3B

```
 946 ATGGCTATTGCTACTGGTGGTGCAGTGTTTGGAGAGAGGGATTGACCCTGAATCTTGAAGACGTTCAGCCTCATGACTTAGGAAAAGTT   345
     MetAlaIleAlaThrGlyGlyAlaValPagGlyGluGluThrLeuAsnLeuGluAspValGlnProHisAspLeuGlyLysVal
1036 GGAGAGGTCATTGTGACCAAAGACGATGCCATGCCAAGGCTCAAATTGAAAAACGTATTCAAGAATCATT                     375
     GlyGluValIleValThrLysAspAspAlaMetLeuLeuLysGlyLysAlaGlnIleGluLysArgIleGluIleIle
1126 GAGCAGTTAGATGTCACAACTAGTGAATATGAAAAGGAAAAACTGAATGAACGGCTTGCAAACTTTGAGGAGTGGCTGTGCTGAAG    405
     GluGlnLeuAspValThrThrSerGluTyrGluLysGluLysLeuAsnGluArgLeuAlaLysLeuSerAspGlyValAlaValLeuLys
1216 GTTGGTGGGACAAGTGATGTTGAAGTGAATGAAAAGAAAAGACAGAGTTACAGATGCCCTTAATGCTACAAGAGCTGCTGTTGAAGAAGGC  435
     ValGlyGlyThrSerAspValGluValAsnGluLysLysArgGlnSerTyrArgValThrAspAlaLeuAsnAlaThrArgAlaAlaValGluGluGly
1306 ATTGTTTTGGGAGGGGTTGTGCCCTCCTCGATGCATTCCAGCCCTTGACTCATTGACTTCAGCTAATGAAGATCAAAAAATTGGTATA     465
     IleValLeuGlyGlyValValProSerSerLeuThrProAlaLeuAspSerLeuThrProAlaAsnGluAspGlnLysIleGlyIle
1396 GAAATTATTAAAAGAACACTCAAAATTCCAGCAATGCTAAGAATGCCAATGCAGGTGTTGAAGGATCTTTGATAGTTGAGAAAATTATG    495
     GluIleIleLysArgThrLeuLysIleProAlaMetThrIleAlaLysAsnAlaGlyValGluGlySerLeuIleValGluLysIleMet
1486 CAAAGTTCCTCAGAAGTTGGTTATGATGCTATGGCTGGAGATTTTGTGAATATGGTGAAAAAGGAATCATTGACCCCAACAAAGGTTGTG   525
     GlnSerSerSerGluValGlyTyrAspAlaMetAlaGlyAspPheValAsnMetValGluLysGlyIleIleAspProThrLysValVal
1576 AGAACTGCTTTATTGGATGCTGCTGGTGTGGCCTCTCTGTTAACTACAGCAGAAGTTGTAGTCACAGAAATTCCTAAAGAAGAAGAAGAC   555
     ArgThrAlaLeuLeuAspAlaAlaGlyValAlaSerLeuLeuThrThrAlaGluValValValThrGluIleProLysGluGluAspAsp
1666 CCTGGAATGGGTGCAATGGGTGGAGGTGGAATGGGAGGTGGTATGGGAGGTGGCATGTTCTAACTCCTAGACTAGTGCTTTACCTTTATTAATGAA  573
     ProGlyMetGlyAlaMetGlyGlyGlyMetGlyGlyGlyMetGlyGlyGlyMetPheEnd
1756 CTGTGACAGGAAGCCCAAGGCAGTGTTCCTCACCAATAACTTCAGGAGAAGTCAGTGGAGAAAATGAAGAAAAAGGCTGGCTGAAAATCA
1846 CTATAACCATCAGTTACTGGTTCAGTTGACAAAATATATAATGGTTACTGCTGTCATTGTCCATGCCTACAGATAATTATTTTGTAT
1936 TTTTGAATAAAAACATTTGTACTACAAATCCTGATACTGGGTACAAGAGCCATGTACCAGTGTACTGCTTTCAACTTAAATCACTGAGGCATT
2026 TTTACTACTATTCGTTAAATCAGATTTTAGTGCTTGCCACCACAGAGAAGTTAAGCAGCCTTTCTGTGGAGAGTGAGAATAAT
2116 TGTGTACAAAGTAGAGAAGTATCCAATTATGTGACAACCTTTGTTAATAAAAATTTGTTAAAGTTAAAAAAAAAAAAAAA
```

T CELL RESPONSE TO p277 PEPTIDE OF HUMAN hsp65 ANTIGEN

T CELL RESPONSE TO hsp65 AND p277

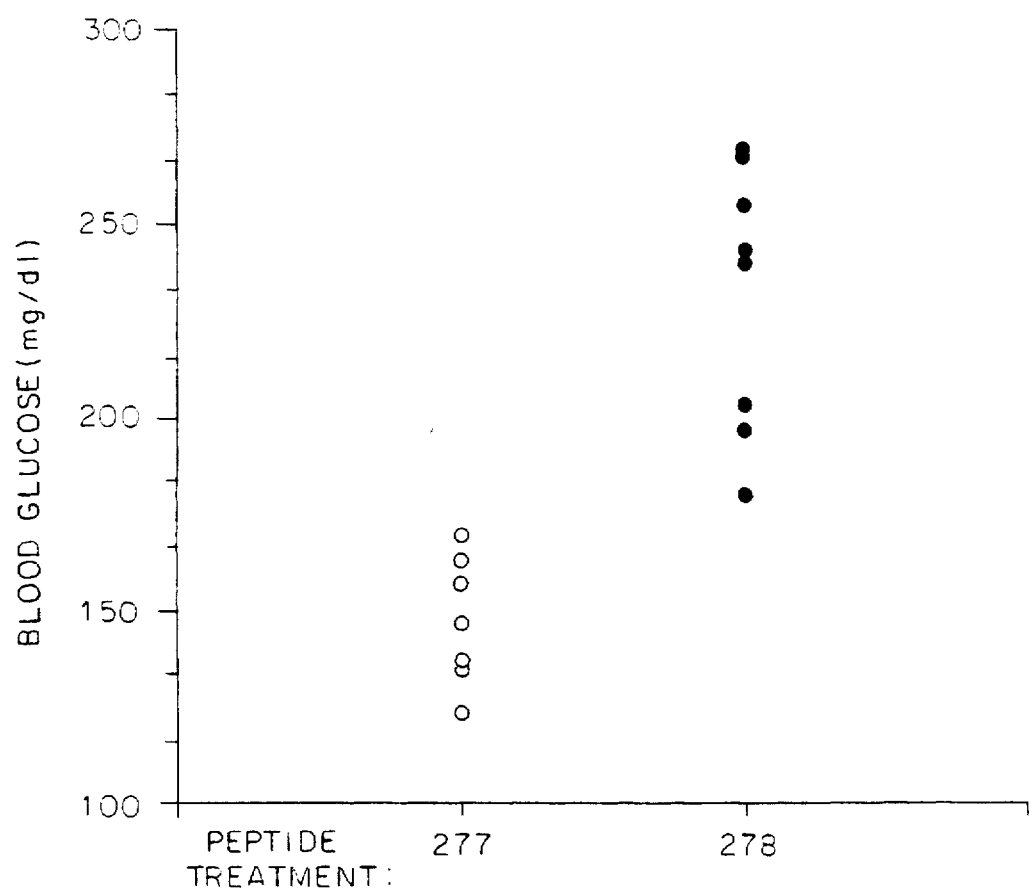

DIAGNOSIS AND TREATMENT OF INSULIN DEPENDENT DIABETES MELLITUS USING HEAT SHOCK PROTEIN DETERMINENTS

CROSS-REFERENCE TO RELATED APPLICATION

The present application is a continuation of application Ser. No. 07/937,449, now abandoned, filed Aug. 31, 1992; which is a continuation of application Ser. No. 07/493,127, filed Mar. 14, 1990, now abandoned, which is a continuation-in-part of application Ser. No. 07/371,249, filed Jun. 26, 1989, now U.S. Pat. No. 5,114,844, which in turn was a continuation-in-part of application Ser. No. 07/322,864, filed Mar. 14, 1989, now abandoned the entire contents of each of which are hereby incorporated by reference.

FIELD OF THE INVENTION

The present invention relates to a method for detecting the existence of, a tendency to develop, or the initiation of a process leading to insulin dependent diabetes mellitus (IDDM), and, more particularly, to such a method which detects the presence of a 65 KD heat shock protein (hsp65) (or a molecule immunologically cross-reactive therewith) or antibodies or T cells reactive with such a protein.

The present invention further relates to a method for the prevention of IDDM or the treatment of IDDM in its incipient stages by administering hsp65 or an immunologically related protein or fragment, or by administering T cells activated by such protein or fragment, such T cells which have been treated to attenuate them or improve their immunogenicity, or fragments of such T cells or treated T cells, in such a manner as to cause immunological tolerance therefor.

BACKGROUND OF THE INVENTION

The incidence of insulin dependent diabetes mellitus (IDDM) has risen several fold during recent decades in many countries and it is estimated that 1% of the people alive today will have developed IDDM before they reach the age of 70. IDDM is caused by an autoimmune process which destroys the insulin-producing beta cells. Diabetes becomes clinically evident only after the vast majority of beta cells are irrevocably destroyed (perhaps 90%) and the life of the individual becomes dependent on an exogenous supply of insulin. In other words, at the time of clinical diagnosis, the autoimmune process has already done irreversible damage, most of it without noticeable symptoms.

Successful treatment of the autoimmune process responsible for the disease ideally should be initiated before the patient has overt symptoms of diabetes and requires insulin replacement for his or her own lost capability to produce insulin. Termination of the autoimmune process would result in cure of the disease and prevention of the need for exogenous insulin only if the disease process could be halted while the patient still possessed a sufficient number of beta cells to provide adequate amounts of endogenous insulin. Therefore, any form of therapy would be more effective if persons at risk could be identified while they were yet without overt symptoms of IDDM and before the patients require exogenous insulin. About 90% of new cases of IDDM occur outside of families with known cases. Therefore, assays suitable for mass screening are urgently needed to detect the subclinical disease process at a stage before it is irreversible.

Fortunately, there are a variety of animal models for IDDM, including BB rats and NOD mice (for example, see Rossini et al., Ann. Rev. Immunol., 3:289–320, 1985). Many of the animals develop autoimmune IDDM spontaneously, and demonstrate many of the features of IDDM in humans.

Heat shock proteins (hsp's) are a family of proteins produced by cells exposed to elevated temperatures or other stresses. The hsp's include proteins of various molecular weights, including 20 KD, 65–68 KD, 70 KD, 90 KD, 110 KD, and others. The heat shock proteins are ubiquitous throughout nature; they are produced by bacteria, yeasts, plants, insects, and higher animals, including humans. The hsp protein molecules are highly conserved and show remarkable homology among all of these diverse creatures. Because of their extreme conservation over evolutionary time, heat shock proteins are thought to perform vital functions. They usually exhibit increased synthesis following exposure of cells to stressful stimuli including heat, certain metals, drugs, or amino acid analogues. Nevertheless, the special functions of these proteins so far are obscure.

For example, patients with systemic lupus erythematosus (SLE) were observed to have antibodies to a 90 KD heat shock protein (Minota et al., J. Clin. Invest., 81:106–109, 1988). The function of these antibodies to hsp90 are not known.

Hsp65 was found to be involved in adjuvant arthritis in rats, cf. van Eden et al., Nature, 331:171–173, 1988. Adjuvant arthritis is an autoimmune arthritis triggered by immunizing certain strains of rats to Mycobacterium tuberculosis (MT) organisms. It was found that the disease could be transferred to immunologically naive, irradiated rats by a clone of T-lymphocytes reactive to a 9 amino acid peptide sequence (180–188) of the hsp65 of MT (hereinafter MT hsp65). Thus, adjuvant arthritis appeared to be an autoimmune disease produced by anti-hsp65 T-lymphocytes. The autoimmune attack against the joints was attributed to partial sequence homology between the 180–185 hsp65 peptide and a segment of the link protein of the cartilage proteoglycan (cf. Cohen, Scientific American, 256:52–60, 1988). It was also found that T-lymphocytes from the synovial fluids of patients with rheumatoid arthritis responded to the hsp65 of MT (cf. Res et al., Lancet, II:478–480, 1988).

Administration of hsp65 to rats before induction of adjuvant arthritis was found to prevent the later development of arthritis. Thus, the presence of an immune response to hsp65 was associated with arthritis in both rats and humans, and administration of hsp65 could lead to resistance to arthritis.

European patent application 262,710 discloses polypeptides useful for alleviation, treatment, and diagnosis of autoimmune arthritis and similar autoimmune diseases.

The complete primary structure, including nucleotide and deduced amino acid sequence of the human P1 protein has recently been published in Jindal, S. et al, "Primary Structure of a Human Mitochondrial Protein Homologous to the Bacterial and Plant Chaperonins and to the 65-Kilodalton Mycobacterial Antigen," Molecular and Cellular Biology, 9, 5, 2279–2283, 1989. This protein, disclosed as having a molecular weight of about 63 kDa, is the human heat shock protein referred to herein as the hHSP65 protein. The entire contents of this publication are hereby incorporated herein by reference. The structure of this protein reproduced as FIG. 3 herein is intended to be identical to that disclosed in Jindal.

European patent application 261,648 discloses the use of activated T cells specific for an autoimmune disease for the treatment of such disease. The T cells are preferably first pressure treated, subjected to a chemical cross-linking agent and/or subjected to a cytoskeletal disrupting agent in order to improve their immunogenicity. The entire treated cell or fraction thereof may be used as a vaccine against the autoimmune disease for which the T cell is specific.

In the known procedure for causing the arrest of autoimmune T cells, the subject is immunized with a sample of attenuated or avirulent T cells of the particular autoimmune specificity, or fragments or fractions thereof. The subject responds by activating regulatory T cells of at least two types: anti-ergotypic T cells that recognize T cell activation markers and anti-idiotypic T cells that appear to recognize the self-antigen receptors present on the pathogenic endogenous autoimmune T cells. T cell vaccination in experimental animals is effective in inducing permanent remission of established disease as well as in preventing disease. Howell et al. *Science*, 246:668–670, 1989, and Vandenbark et al. *Nature*, 341:541–544, 1989, disclose use of peptide sequences of a T cell receptor β chain for vaccination of rats against experimental autoimmune encephalomyelitis, thereby supporting the conclusion that the autoimmune T cell receptor itself can supply a target epitope for regulator T cells.

While such use of T cells or fragments was known for autoimmune diseases in general, the particular antigen specific for IDDM was not previously known and, thus, activated T cells for vaccination against IDDM were not obtainable prior to the present invention.

SUMMARY OF THE INVENTION

It is an object of the present invention to provide methods for the early diagnosis of insulin dependent diabetes mellitus (IDDM).

It is a further object of the present invention to provide kits for use in the early diagnosis of IDDM.

It is another object of the present invention to provide methods for the prevention of IDDM.

It is yet another object of the present invention to provide methods for the treatment of IDDM in its incipient stages.

It is still a further object of the present invention to provide tolerogenic compositions for the prevention or treatment of IDDM.

It is yet a further object of the present invention to provide polypeptides which can be used for the prevention or treatment of IDDM.

It is still another object of the present invention to provide T cells or fragments useful for the prevention of IDDM or treatment of IDDM in its incipient stages.

It is a further object of the present invention to use the IDDM specific antigen of the present invention to isolate T cells specific thereto and then to characterize the peptide sequence of the receptor region of such T cells and use such receptor peptides for the prevention or treatment of IDDM.

According to the discovery of the present invention, in the course of developing IDDM, animals express hsp65 molecules, or molecules which are cross-reactive therewith, which find their way into the blood and urine of the animals. They also express antibodies and T cells directed specifically to such molecules. Thus, the presence of hsp65 (or molecules which are cross-reactive therewith) or antibodies or T cells specific thereto in blood or urine, serves as an assay for the detection of the IDDM process before the destruction of beta cells is completed and the individual is doomed to life-long diabetes.

The presence or incipience of IDDM in a patient can be diagnosed by testing for the presence of hsp65 (or molecules which are cross-reactive therewith) or antibodies or T cells specific thereto.

The present invention also relates to means for performing such assays, as well as kits for performing such assays. The detection of incipient diabetes then permits a patient to begin measures aimed at terminating the autoimmune process. For example, the administration of hsp65, or an active epitope thereof or another molecule (antigen) which is immunologically cross-reactive therewith, is effective in inducing resistance to the autoimmune process involved in IDDM. Administration of T cells specific to such antigens, in attenuated or avirulent form or after having been treated to improve their antigenicity, or fragments or active fractions thereof, will also serve to induce resistance to the autoimmune process involved in IDDM.

The present invention further relates to means for preventing or treating IDDM. It has been discovered that immunization to hsp65, or the active epitope thereof or another molecule (antigen) which is immunologically cross-reactive therewith, in an appropriate adjuvant can induce IDDM. However, vaccination with such an antigen, without an effective adjuvant, and preferably with a "tolerogenic carrier", can produce a specific tolerance to the antigen. This effectively creates a resistance to the autoimmune process of IDDM. The same is true with respect to vaccination with T cells specific to such antigens, in attenuated or avirulent form or after having been treated to improve their antigenicity, or fragments or active fractions thereof. If the patient is shown to already be in the pre-clinical incipient stages of IDDM, injection with such an antigen or T cell (or fraction) can create a tolerance for this antigen and thus arrest the autoimmune process before significant, permanent damage is done.

BRIEF DESCRIPTION OF THE DRAWINGS

The present invention will be better understood from the following brief description of the drawings and the subsequent detailed description of the preferred embodiments.

FIG. 3 shows the nucleotide and deduced amino acid sequences of the human P1 protein, which is an hHSP65. Numbers on the left refer to the nucleotide sequence relative to coordinate 1 at the beginning of the putative initiation codon. The amino acid sequence is numbered starting with 1 at the same point. The 5' extension of this reading frame is shown in one-letter code. The position of the internal EcoRI site (nt 712), which marks the beginning of the λ22a sequence, is indicated. The polyadenylation signal 15 nt from the A tail at the 3' end is underlined. The putative mitochondrial targeting sequence at the N-terminal end and a keratin-like amino acid sequence at the C-terminal end containing repeats of Gly-Gly-Met are boxed. Positively charged amino acids in the leader sequence are identified (+).

FIG. 7 shows the results of immunization against peptides p277 and p278 in resisting induced diabetes. The dots show the blood glucose level three weeks after immunization for each mouse in the test groups.

DETAILED DESCRIPTION OF PREFERRED EMBODIMENTS

Figure 1:
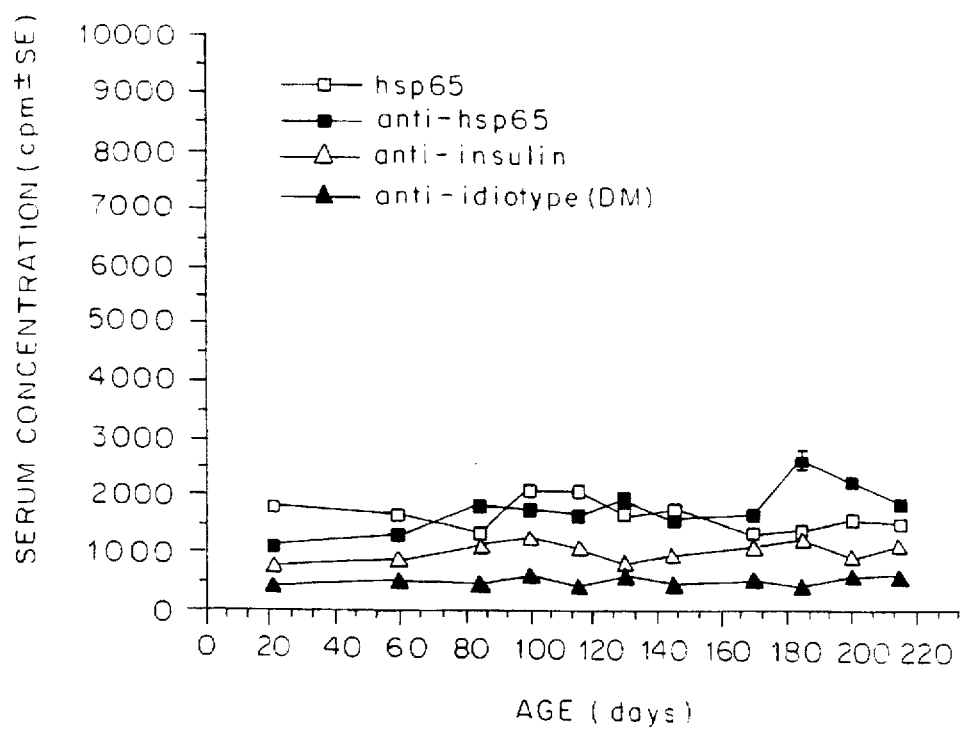
FIG. 1 shows the amounts of hsp65, anti-hsp65 antibody, anti-insulin antibody, and anti-idiotypic antibody in the serum of NOD mice that did not develop IDDM.

The following examples show specific embodiments of the present invention and experiments relating to the present invention. These are intended as examples only and are presented in a non-limitative manner.

EXAMPLE 1

Production of the MT hsp65 Molecule

The hsp molecule of *Mycobacterium tuberculosis* was transfected into *E. coli* by standard procedures and purified as described by van Eden et al, *Nature*, 331:171-173, 1988. Such genetically engineered *E. coli* cells will produce substantial quantities of MT hsp65. Because of the close homology between hsp's of various sources, hsp65 of mammalian or human origin is also effective when produced by genetic engineering or isolation from cells.

EXAMPLE 2

Production of Antibodies to MT hsp65

Rabbits of a standard laboratory strain (New Zealand White) were inoculated subcutaneously in the back with 100 micrograms of MT hsp65 produced in accordance with Example 1, in 0.5 ml saline emulsified in 0.5 ml mineral oil (incomplete adjuvant). One month later the rabbits were boosted with 100 micrograms of MT hsp65 in 1.0 ml saline, and two weeks later the rabbits were bled and the serum collected. The rabbits were boosted in a similar manner after two months and bled again. The sera antibodies were used to detect hsp65 in the blood and urine of test animals and humans.

EXAMPLE 3

Assay of hsp65

A standard solid phase radioimmunoassay is used to detect the presence of hsp65 molecule. Flexible PVC microtiter plates are coated with 100 µl test serum or urine for 18 hours at 4° C. and washed with phosphate buffered saline (PBS). Control rabbit serum or anti-hsp65 serum (produced in accordance with Example 2) is then diluted 1:100 in PBS+0.1% bovine serum albumin (BSA), and 50 µl is added to each well and incubated for 2–3 hours at 37° C. The wells are then washed three times in PBS. $^{125}$I-goat anti-rabbit Ig, 100,000 cpm/well, is added and the wells are maintained for two hours at 37° C. The plates are then washed four times in PBS and dried, and the wells are counted in a gamma counter. Values obtained with anti-hsp65 serum 2 S.D. above the mean cpm obtained with normal rabbit serum are considered as positive for the presence of hsp65.

EXAMPLE 4

Assay of Anti-hsp65 Antibodies

Antibodies to hsp65 are detected in a similar fashion except that the antigen bound to the plates is not test serum or urine, but purified MT hsp65 produced in accordance with Example 1, 5 µm/well. The serum to be tested for anti-hsp65 antibodies is diluted 1:50. Urine is used undiluted. The serum or urine is added to the wells containing MT hsp65 and the presence of antibodies binding to MT hsp65 is detected using radiolabelled goat anti-mouse Ig for mouse specimens and goat anti-human Ig for human specimens. The remainder of the assay is done as described in Example 3. Positive results are defined as cpm greater than 2 S.D. above the mean cpm obtained using control sera from healthy mice, rats, or humans.

EXAMPLE 5 hsp65 Molecules and Anti-hsp65 Antibodies Detect Development of IDDM Before Its Onset NOD Mice Fourteen female NOD mice were bled beginning on day 21 of life at regular intervals for about 200 days and scored for the development of IDDM. The sera were tested for hsp65, anti-hsp65 antibodies, anti-insulin antibodies, and anti-idiotypic antibodies to DM idiotype.

The levels of hsp65 in mice were tested using the assay of Example 3. The presence of anti-hsp65 antibodies was assayed according to the procedure of Example 4. Anti-insulin antibodies are idiotypic antibodies which recognize the receptor binding sites of insulin, sometimes designated DM-idiotypic antibodies. Anti-idiotypic antibodies are antibodies against DM-idiotypic antibodies, sometimes designated anti-DM-idiotypic antibodies. In U.S. application Ser. No. 07/295,401 (now abandoned, corresponding to EP 234, 687), owned by the present assignee, it is disclosed that the presence of DM-idiotypic antibodies or anti-DM-idiotypic antibodies in the serum or urine of a patient is a positive indication of incipient or active IDDM. Such antibodies are not present in the serum or urine of healthy patients. The procedures used to assay for the presence of anti-insulin antibodies and anti-idiotypic antibodies are as set forth in said Ser. No. 07/295,401, the entire contents of which are hereby incorporated herein by reference.

Figure 2:
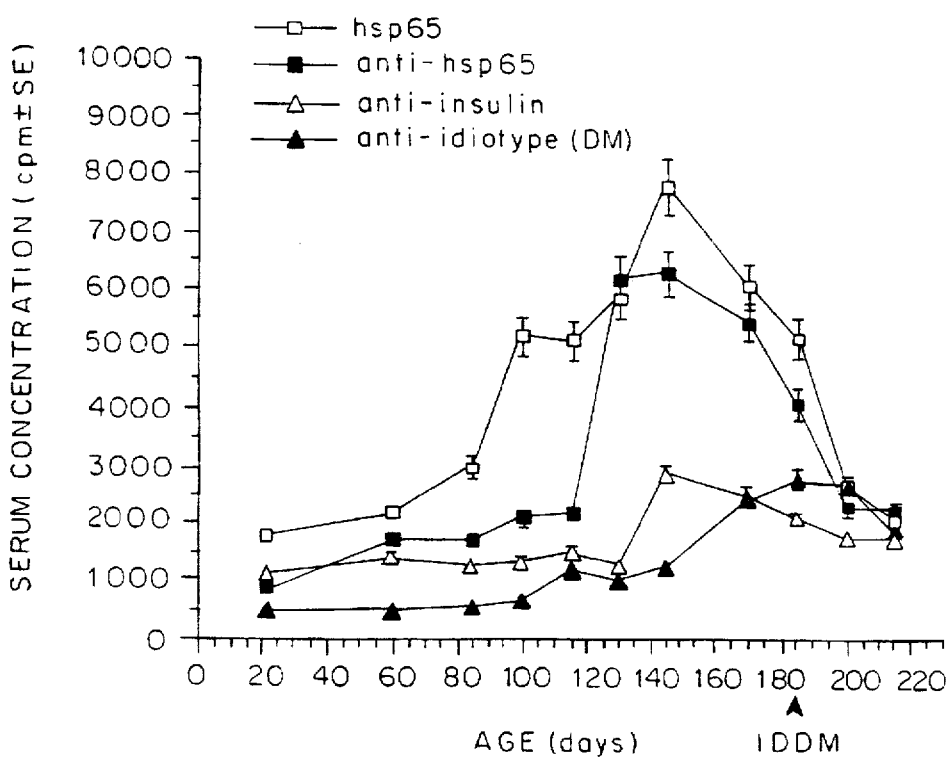
FIG. 2 is a graph showing that marked increases in hsp65 and anti-hsp65 antibodies precede the development of overt IDDM in NOD mice that did develop the disease. Anti-insulin and idiotypic (DM) antibodies preceded IDDM by a lesser extent.

Ten of the NOD mice developed IDDM and four remained free of IDDM. FIG. 1 shows the results of testing the sera of one mouse that did not develop IDDM, and FIG. 2 shows the results of testing the sera of one of the mice that did develop IDDM. It can be seen that compared to the IDDM-free mouse, the mouse that did develop IDDM on day 185 of life developed a markedly elevated concentration of hsp65 beginning on day 85. The hsp65 concentration decreased after IDDM actually appeared. Anti-hsp65 antibodies appeared several weeks after the appearance of hsp65. Anti-insulin and anti-idiotypic (DM) antibodies appeared much later. Thus, elevation of levels of hsp65 and the anti-hsp65 antibodies preceded clinical IDDM and served as early signs of the subclinical disease process.

Table 1 shows the cumulative data obtained from the fourteen individual mice.

TABLE 1

Serum Assay of Impending IDDM in NOD Mice

| Mouse | Day of IDDM onset | Days Positive Test Preceded IDDM Onset | | | |
|---|---|---|---|---|---|
| | | hsp65 | anti-hsp65 antibodies | anti-insulin antibodies | anti-idiotype antibodies |
| 1 | none | 0 | 0 | 0 | 0 |
| 2 | none | 0 | 0 | 0 | 0 |
| 3 | none | 0 | 0 | 0 | 0 |
| 4 | none | 0 | 0 | 0 | 0 |
| 5 | 185 | 90 | 45 | 45 | 30 |
| 6 | 185 | 100 | 50 | 45 | 20 |
| 7 | 170 | 90 | 60 | 60 | 30 |
| 8 | 170 | 100 | 50 | 30 | 20 |
| 9 | 145 | 60 | 60 | 25 | 15 |
| 10 | 145 | 70 | 30 | 15 | 15 |
| 11 | 145 | 60 | 40 | 20 | 20 |
| 12 | 130 | 50 | 20 | 0 | 0 |
| 13 | 115 | 55 | 55 | 20 | 20 |
| 14 | 115 | 50 | 30 | 30 | 20 |
| Mean | 150.5 | 72.5 | 44 | 29 | 19 |
| SE | 8.28 | 6.47 | 4.33 | 5.47 | 2.67 |
| Median | 145 | 65 | 47.5 | 27.5 | 20 |

The mean age of IDDM onset was 150.5 days in the mice developing disease. The mean hsp65 serum test was positive 72.5 days before IDDM and the mean anti-hsp65 antibody test was positive 44 days before IDDM. The anti-insulin and anti-idiotypic antibody tests were positive only 29 and 19 days before IDDM on the average. The tests were not significantly positive in mice escaping IDDM. Therefore, hsp65 and anti-hsp65 antibodies are relatively early indicators of eventual development of IDDM.

Urine was tested for the presence of hsp65 in the NOD mice at about 100 days of age. Table 2 shows that the urine of the mice tested positive in those mice that did develop IDDM.

TABLE 2

Urine Assay of Impending IDDM in NOD Mice

| IDDM | Urines positive for hsp65 |
|---|---|
| Yes | 10/10 |
| No | 0/4 |

Table 3 shows that BB rats that did not develop IDDM did not manifest hsp65 or anti-hsp65 antibodies in the serum or urine. Rats that did develop IDDM (on days 90–100) were positive when tested 10 to 20 days before the outbreak of IDDM. The assays were conducted as disclosed in Examples 3 and 4.

TABLE 3

Assays of hsp65 and Anti-hsp65 antibodies Associated with Development of IDDM in BB Rats

| Development of IDDM | Serum | | Urine | |
|---|---|---|---|---|
| | hsp65 | anti-hsp65 | hsp65 | anti-hsp65 |
| Yes | 10/10 | 5/5 | 4/5 | 3/5 |
| No | 0/5 | 0/5 | 0/5 | 0/5 |

Human IDDM Patients

Sera were available from five patients at various times before they developed IDDM. The sera were obtained from these persons ½ to 2 years before the onset of IDDM because they were first degree relatives of known IDDM patients and were thought to be at risk of developing IDDM themselves.

In addition to those persons, sera and urines of four newly diagnosed IDDM patients were studied for hsp65. Control sera and urines were obtained from 10 patients with active multiple sclerosis and 35 children seen at a general hospital for a variety of problems not related to IDDM. The results are shown in Table 4. The assays were conducted in accordance with the procedures of Examples 3 and 4.

TABLE 4 hHSP65 and anti-hHSP65 antibodies in human IDDM patients

| Humans | Serum | | Urine | |
|---|---|---|---|---|
| | hHSP65 | anti-hHSP65 | hHSP65 | anti-hHSP65 |
| Pre-IDDM | 4/5 | 4/5 | N.D. | N.D. |
| New IDDM | 2/4 | 2/4 | 2/4 | 2/4 |
| Multiple Sclerosis | 0/10 | 0/10 | N.D. | N.D. |
| Hospitalized Children (no IDDM) | 0/35 | 0/35 | N.D. | N.D. |
| Healthy adults | 0/10 | 0/10 | 0/10 | 0/10 |

It can be seen from the above table that four out of five of the pre-IDDM patents and two out of four of the IDDM patients were positive in the hHSP65 and anti-hHSP65 antibody assays. None of the controls was positive. Thus, anti-hsp65 antibodies raised in rabbits against hsp65 of MT can detect hHSP65 in human serum and urine in association with the development of IDDM. Moreover, hsp65 of MT could detect human antibodies. As discussed above, antibodies made to hsp65 of human or other origin can also be used in these assays, as well as hsp65 obtained from human or other sources. This is possible because of the high degree of conservation of hsp's throughout biological evolution.

That all of the pre-IDDM and new IDDM patients were not positive is explained by the fact that the concentrations of hHSP65 and anti-hHSP65 antibodies tend to decrease at or around the actual time of IDDM onset, as shown in FIG. 2. Thus, the negative patients may have lost their positivity when they were tested close to the onset of IDDM.

From the above, it is apparent that human patients will be positive for hHSP65 (or a molecule cross-reactive therewith) or anti-hHSP65 antibodies at some time early before the onset of IDDM. Assays for hHSP65 or anti-hHSP65 antibodies are therefore useful in screening populations for those that may be in the process of developing IDDM.

The hHSP65 appearing in the blood or urine of individuals developing IDDM could come from several sources. The sources may be hHSP65 expressed normally by healthy beta cells and released when the beta cells undergo viral infection or toxic insult as a prelude to immunological destruction, or it may be released from the beta cells by the stress of immunological destruction. The hHSP65 might also be expressed by the cells of the immune system during their prolonged activity against the beta cells. Although the sources of hHSP65 in the system are not at this time conclusively known, it has been determined that once the hHSP65 is released, the individual is stimulated to make antibodies to the hHSP65 molecule.

Antibodies to an undefined molecule of 64,000 Da molecular weight have been described in some newly diagnosed IDDM patients by Baekeskov et al. in Nature, 298: 167–168, 1982. However, it is not known whether the 64 KD antigen is an hsp. Moreover, the 64 KDa antigen is not known to appear in blood or urine before the onset of IDDM.

In contrast to this undefined 64 KD beta cell antigen, MT hsp65 is a defined protein whose amino acid sequence is known (Thole et al. *Infection and Immunity*, 55:1466–1475, 1987). Similarly, the amino acid sequence of hHSP65 is shown and set forth in FIG. 3.

EXAMPLE 6

Study of Male Mice of Strain C57BL/Ksj

C57BL/Ksj mice develop IDDM approximately two weeks after receiving five consecutive daily inoculations of the beta cell toxin streptozotocin at doses of 40 mg/kg per day.

In the experiments described herein, groups of ten male C57BL/Ksj mice, aged 3 months, were or were not subjected to low-dose streptozotocin injections (40 mg/kg daily×5) to induce IDDM (appearing at day 14) and were investigated for the development of IDDM, as measured by blood glucose higher than 250 mg %, and for the appearance of hsp65 and anti-hsp65 antibodies in the blood. As shown in Table 5, the hsp65 appeared by day 10 (before clinical manifestation of IDDM), followed by anti-hsp65 antibodies.

TABLE 5

Low-dose streptozotocin model of IDDM in C57Bl/ksj mice:
Induction of hsp65 and anti-hsp65 antibodies

| Appearance of | Streptozotocin | IDDM Cumulative Incidence on Days | | | |
|---|---|---|---|---|---|
| | | 0 | 5 | 10 | 25 |
| IDDM | Yes | 0 | 0 | 0 | 100 |
| | No | 0 | 0 | 0 | 0 |
| hsp65 | Yes | 0 | 0 | 90 | 100 |
| | No | 0 | 0 | 0 | 0 |
| anti-hsp65 | Yes | 0 | 0 | 0 | 90 |
| | No | 0 | 0 | 0 | 0 |

EXAMPLE 7

Multiple Murine Molecules are Cross-reactive with hsp65 of Mycobacteria

To identify the mammalian molecules recognized by antibodies to mycobacterial hsp65, the rabbit anti-MT hsp65 antiserum described above was tested, as was a monoclonal antibody designated as TB78. This antibody was developed and supplied by Dr. J. Ivanyi, of the MRC Tuberculosis Unit, Hammersmith Hospital, London. This antibody is specific for the hsp65 molecule of *M. tuberculosis*. Three types of preparations were assayed for their binding of these antibodies: Cloned hsp65 of *M. tuberculosis*; the sera of NOD mice developing IDDM and healthy controls; and lysates of rat fibroblasts treated with heat shock and control fibroblast lysates.

MT Hsp65 was prepared as described in Example 1. Rat embryonic fibroblasts were cultured using standard procedures. To induce heat shock proteins, cultures of fibroblasts were incubated at 42.5° C. for two hours and then for ½ hour at 37° C. The heat shocked fibroblasts and control fibroblasts were cultured at 37° C., and about 5×10⁶ cells each were then lysed using a lysis buffer composed of 0.1% SDS and 1% Triton together with protease inhibitors. The protein concentration was adjusted by Bradford determination to 2 mg/ml. The material was run in 10% polyacrylamide gel, 100 micrograms per lane, for standard electrophoresis, under reducing conditions (2% 2-mercaptoethanol). Mouse sera from healthy control mice and from NOD mice developing IDDM were diluted to a concentration of 2 mg/ml. Each of these serum preparations was separated by polyacrylamide gel electrophoresis as above. The separated proteins were then transferred overnight to nitrocellulose paper by standard procedures. The papers were then incubated for one hour at room temperature with 1% hemoglobin (for blocking) and then with either normal rabbit serum or anti-hsp65 antibody at a dilution of 1:100, or with TB 78 or a control monoclonal antibody at dilutions of 1:100 for two hours at room temperature. Binding of the antibodies to any of the separated bands was detected by incubation with $^{125}$I-radiolabelled goat anti-rabbit Ig or goat anti-mouse Ig, washed and developed by autoradiography. Molecular weight standards were included.

It was found that several bands were detected by the anti-hsp65 antibodies. Mycobacterial hsp65 was detected by both the rabbit antiserum and monoclonal TB68. The antibodies also recognized a 65 KD band in the murine fibroblasts that was expressed in an augmented fashion after heat shock. In the heated fibroblast lysates there were also positive bands at 30 KD and 47 KD. An additional band at about 25 KD was detected in the sera from the NOD mice developing IDDM. Therefore, mammalian molecules of 65 KD, 47 KD, 30 KD and 25 KD are cross-reactive with mycobacterial hsp65.

EXAMPLE 8

Hsp65 is Expressed in the Islets of the Pancreas

Because the development of IDDM is accompanied by augmented levels of hsp65 in the blood and urine, it was thought that the beta cells in the islets might be the source of the hsp65. In order to test this theory, rabbit anti-hsp65 were tested to see if they would bind to islet cells.

A standard procedure was used to prepare frozen sections of rat pancreas, 6–8 microns thick. The sections were overlaid with normal rabbit serum or anti-MT hsp65 antiserum (absorbed with liver powder to remove non-specific antibodies) diluted 1:50 and incubated for 30 minutes at room temperature, thoroughly washed with PBS, and then incubated for 5 minutes with 5% normal goat serum before incubation with fluorescein labelled goat anti-rabbit Ig for 30 minutes at room temperature, washed with PBS and examined using a fluorescence microscope. The islets were brightly stained by the anti-hsp65 antiserum, but not by the control rabbit serum. Therefore, islets express hsp65.

EXAMPLE 9

Immunization to hsp65 Induces IDDM

Since it was found that islet cells express hsp65, it was postulated that an anti-hsp65 immune response would damage beta cells and thereby induce IDDM. Male C57BL/Ksj mice, 8 weeks old, or female NOD mice, 4.5 weeks old, were immunized by intraperitoneal injection with 50 µg of MT hsp65 and tested as to whether they might develop IDDM, as evidenced by blood glucose greater than 250 mg %. At 4.5 weeks of age, the NOD mice were at least three months before spontaneous IDDM. The C57BL/Ksj mice do not develop spontaneous IDDM. The MT hsp65 was administered emulsified in oil or in PBS. Bovine serum albumin (BSA) emulsified in oil was used as a control. The results are shown in Table 6. It was found that MT hsp65 in oil, but not in PBS, induced IDDM. Therefore, an immune response to MT hsp65 can trigger IDDM, probably because the beta cells express an antigen cross-reactive with MT hsp65.

TABLE 6

MT hsp65 in Adjuvant Induces IDDM

| mice | antigen | adjuvant | Incidence of IDDM 3 weeks later |
|---|---|---|---|
| NOD | hsp65 | oil | 7/10 |
|  | hsp65 | PBS | 0/10 |
|  | BSA | oil | 0/20 |
| C57BL/ksj | hsp65 | oil | 6/7 |
|  | hsp65 | PBS | 0/9 |
|  | none | none | 0/15 |

In an additional experiment, strains of normal mice which do not develop IDDM spontaneously, as do NOD mice, or even after low dose streptozotocin, as do C57BL/ksj mice, were inoculated intraperitoneally with 50 µg of antigen, either MT hsp65 or bovine serum antigen (BSA) emulsified in incomplete Freund's adjuvant (oil). The mice were bled in the morning 19 days later and blood glucose was measured. IDDM was diagnosed by a concentration of blood glucose greater than 200 mg %. The results are shown in Table 7. It can be seen that immunization with MT hsp65 can induce IDDM even in some apparently normal strains of mice, particularly when administered in an appropriate dosage. This supports the conclusion that MT hsp65 or molecules immunologically cross-reactive with MT hsp65, are target antigens in IDDM.

TABLE 7

Immunization to MT hsp65 Induces IDDM in Non-Diabetic Strains of Mice

| Mouse Strain | Blood Glucose (mg %) antigens | | IDDM Incidence antigens | |
|---|---|---|---|---|
|  | hsp65 | BSA | hsp65 | BSA |
| C3H.eB/Fej | 270 ± 41 | 96 ± 32 | 5/5 | 0/5 |
| C57BL/6j | 298 ± 52 | 122 ± 26 | 5/5 | 0/5 |
| DBA/2 | 146 ± 33 | 126 ± 21 | 0/5 | 0/5 |
| SJL/j | 162 ± 27 | 139 ± 26 | 0/5 | 0/5 |

EXAMPLE 10

HSP65 Can Induce Resistance to Induction of IDDM

It is well established that antigen administered without an effective adjuvant, or with a tolerogenic carrier, can induce immunological non-responsiveness, i.e., specific tolerance to the antigen. Therefore, mice that had been injected with MT hsp65 in PBS were tested to determine if these mice had acquired resistance to IDDM induced by MT hsp65 in oil. One month after receiving MT hsp65 in PBS, C57BL/Ksj mice were challenged with MT hsp65 in oil, and none of these mice developed IDDM as measured by blood glucose greater than 250 mg % three weeks later. In contrast, 8 of 10 control mice that had not received MT hsp65 in PBS developed IDDM after receiving MT hsp65 in oil.

In another experiment, MT hsp65 was given to 30 day old female NOD mice in PBS, intraperitoneally, 15 days before challenge with 50 µg MT hsp65 in oil to induce IDDM. The presence of IDDM was measured by blood glucose concentration of greater than 200 mg % 35 days after challenge. The presence of IDDM was again measured when the mice were 5 months of age. At this age it is known that 50% of all untreated female NOD mice have detectable IDDM. The results are shown in Table 8.

TABLE 8

Use of MT hsp65 to Vaccinate against IDDM

| MT hsp65 in PBS (µg) | Incidence of IDDM | |
|---|---|---|
|  | 35 days after challenge | 5 months old |
| 0 | 7/8 |  |
| 1 | 0/8 | 0/8 |
| 5 | 0/8 | 0/8 |
| 50 | 0/8 | 0/8 |

Thus, it can be seen that hsp65 can be used to induce tolerance to a diabetogenic immune process. Not only is this tolerance effective with respect to an immunogenic attack of MT hsp65, but it remains effective as a treatment against the natural development of spontaneous IDDM in NOD mice.

EXAMPLE 11

Treatment of Incipient IDDM Using hHSP65

As shown in Example 10, MT hsp65 can be used to induce resistance to the autoimmune process of IDDM. This appears to be caused by a mechanism of immunological tolerance to the hsp65 of the beta cells through exposure to exogenous hsp65. Thus, hsp65 can be useful in treating IDDM before the disease becomes clinically evident and the autoimmune process can be arrested before significant, permanent damage is done. The results of the experiment summarized in Table 8 to the effect that the natural development of spontaneous IDDM in NOD mice can be arrested is significant evidence that hsp65, and particularly hHSP65, can be used therapeutically. The autoimmune process begins very early in NOD mice. At the age of one month insulitis can already be detected. IDDM becomes clinically evident at 5 months in 50% of the female mice of this strain. Administration of hsp65 in 30 day old mice stops this natural development. This establishes that treatment can be effective even after autoimmunity to the islets has already begun.

EXAMPLE 12

T cell Response to hHSP65 is Associated with Developing Diabetes

The human hsp65 (hHSP65) gene shown in FIG. 3 was cloned for expression in a conventional manner and substantially pure recombinant human hsp65 was obtained therefrom.

The present experiment establishes that mice spontaneously destroying their beta cells manifest T cell reactivity to recombinant human hsp65. Spleen cell suspensions obtained from groups of five to seven female NOD/Lt mice of various ages were assayed for T cell proliferation, essentially as described for T cell responses to thyroglobulin (Maron, R. et al., *J. Immunol.*, 131, 2316–2322 (1983)). Briefly, the cells at 1×10$^6$ cells per ml were incubated in triplicate for 72 hours in 0.2 ml of culture medium in microtiter wells in the presence or absence of the following antigens at 5 µg/ml: human hsp65, MT hsp65, or MT hsp70. Proliferation was measured by the incorporation of [$^3$H] thymidine into DNA during the final 12 hours of incubation. The results are shown as the Δ cpm: the mean cpm of the wells containing test antigen minus the mean cpm of the control wells cultured without added antigen±the standard error (SE). The control cpm's varied from 9,000 to 10,500. The onset of IDDM in about 50% of the mice was between 4 and 5 months of age, as marked by "IDDM" in FIG. 4.

Figure 4:
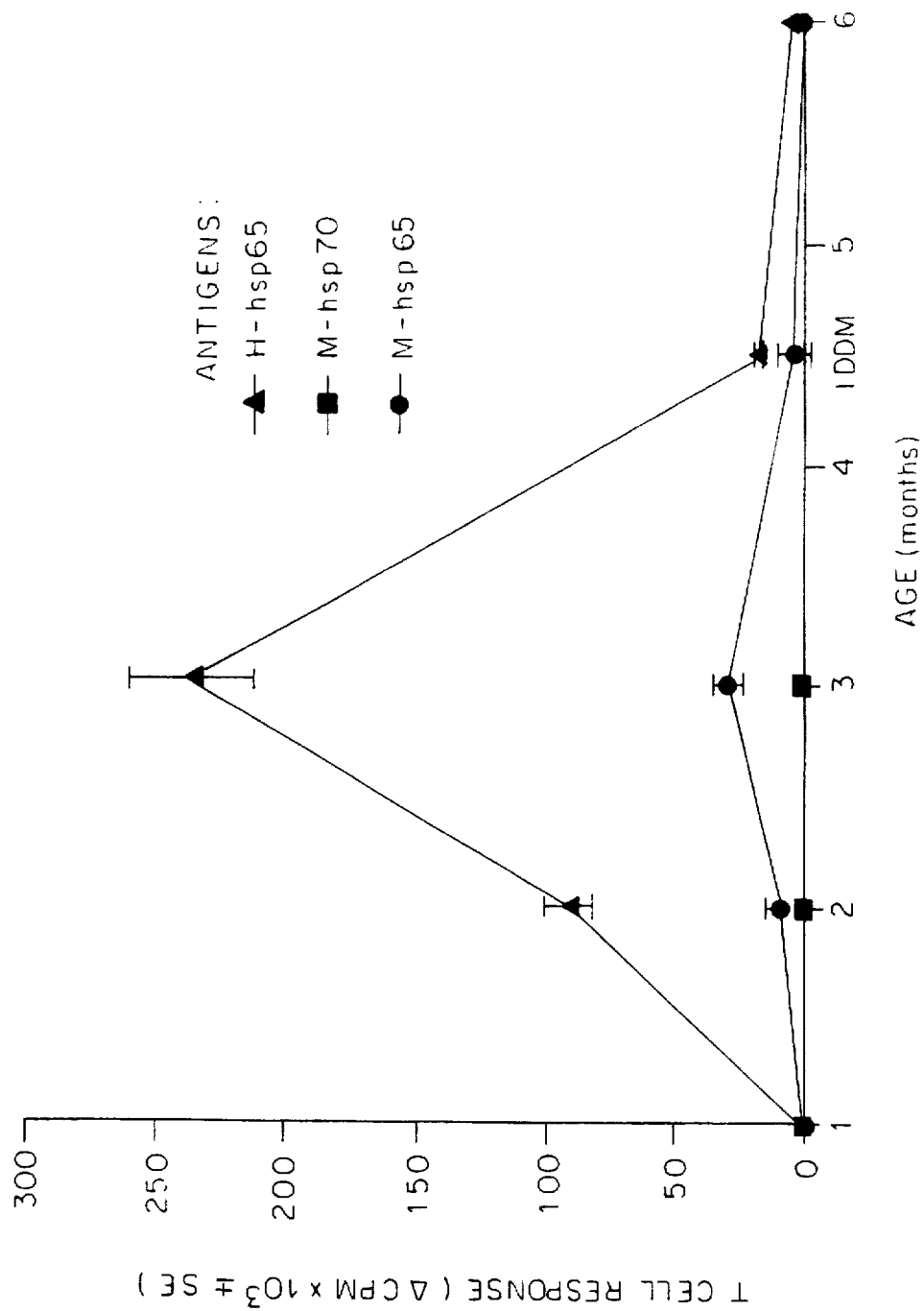
FIG. 4 is a graph showing the degree of spontaneous reactivity of NOD/Lt T cells to human hsp65, MT-hsp65 and MT-hsp70 as a function of age.

The results of this experiment, showing the degree of spontaneous reactivity of NOD/Lt T cells as a function of age to the various antigens, is graphed in FIG. 4. At the age of 1 month when NOD/Lt mice manifest little or no insulitis there was no detectable T cell reactivity to any of the antigens. However, at 2 and 3 months of age, along with increasing insulitis, there was strong and rising reactivity to human hsp65, with relatively lower reactivity to MT hsp65 and no reactivity to MT hsp70. Reactivity to human hsp65 and MT hsp65 declined with the onset of IDDM at 4.5 months and decreased still further at 6 months, after the clinical appearance of IDDM. Thus, the T cell response to human hsp65 appeared to be associated with the increase in the beta cell damage preceding overt IDDM. The fall in T cell reactivity with the outbreak of IDDM can be explained by decreased immune stimulation as the beta cells and their antigens are lost.

EXAMPLE 13

T Cells Responding to Human hsp65 Cause Diabetes

Suspensions of spleen cells were obtained from groups of five 3.5 month old female mice of the strains NOD/Lt, C57BL/6 or C57BL/KS. One group of NOD/Lt mice (Group 2) had been primed 9 days earlier by intraperitoneal immunization with 50 µg/ml of MT hsp65 in oil. Some of the spleen cells (Groups 4, 6 and 8) were activated by incubation for 48 hours with 1.25 µg/ml of Con A. The post-Con A cells were then transferred into growth medium that lacked Con A for an additional 5 days of culture. The spleen cells were tested for their proliferative responses to recombinant human hsp65, recombinant MT hsp65 or to control E. coli antigen a week after activation as described in Example 12. Control E. coli were transfected with the pEX2 plasmid that did not contain the hsp65 genes. The antigens were used at a concentration of 5 µg. Proliferative responses done in triplicate, are shown as the stimulation index (SI): ratio of cpm of $^3$H-thymidine incorporated in the spleen cells incubated with test antigen to the cpm of $^3$H-thymidine incorporated in control cultures without added antigen. The cpm of control cultures were 5000–7000 and the standard deviations from the mean cpm were always less than 10% of the mean. The ability of the cells to produce diabetes was tested by activating some of them by culture with Con A for 48 hours. Groups of prediabetic, one month old female recipient mice were inoculated intraperitoneally with $25 \times 10^6$ naive spleen cells or with Con A activated spleen cells from MT hsp65 primed or naive mice. The recipient mice were scored for the development of acute diabetes 21 days later manifested by hyperglycemia (blood glucose>200 mg/dl) and histologic evidence of insulitis. Blood glucose was measured by removing blood from the tail vein of individual mice at about 9 a.m. and the concentration of glucose was measured using a Diascan Glucose Meter and test strips (Behringwerke, West Germany). Insulitis was determined by histological evidence (hematoxylineosin and light green staining done at the Histology Laboratory of The Weizmann Institute). Grading of insulitis was done by an individual blinded to the identity of the test slides.

The results are set forth in Table 9. The differences between the responses of the NOD/Lt spleen cells to human hsp65 and MT hsp65 (Groups 1–4) were significantly greater (P<0.01) than the responses of NOD/Lt spleen cells to E. coli control antigen or the responses of the other mouse strains (Groups 5–7) to the hsp65 antigens using Student's T test; ND, not determined.

TABLE 9

T Cell Proliferative Responses to H-hsp65 and MT-hsp65

| Group | Mouse Strain | Spleen Cells | Proliferative Responses (SI) To Antigens | | | Transfer of Acute Diabetes | |
|---|---|---|---|---|---|---|---|
| | | | Human hsp65 | MT-hsp65 | E. coli Control | Con A activation | Incidence |
| 1. | NOD/Lt | Naive | 12.4 | 3.5 | 1.0 | No | 0/10 |
| 2. | | MT-hsp65 Primed | 26.8 | 4.7 | 1.3 | Yes | 8/10 |
| 3. | NOD/Lt | Naive | 10.8 | 2.5 | 1.1 | No | 0/10 |
| 4. | | Post-Con A activation | 28.7 | 4.7 | 1.0 | Yes | 8/9 |
| 5. | C57BL/6 | Naive | 1.0 | 1.2 | N.D. | N.D. | N.D. |
| 6. | | Post-Con A activation | 1.1 | 1.1 | N.D. | N.D. | N.D. |
| 7. | C57BL/KS | Naive | 1.0 | 1.0 | N.D. | N.D. | N.D. |
| 8. | | Post-Con A | 1.1 | 0.9 | N.D. | N.D. | N.D. |

The results, set forth in Table 9, show that the T cell responses of 3.5 month old NOD/Lt mice to human hsp65 could be augmented by immunizing the mice to MT hsp65 (Group 2), or by activating the T cell population with the T cell mitogen concanavalin A (Con A; Group 4). Con A has been demonstrated to preferentially stimulate in vitro, activated autoimmune T cells existing in animals in vivo. Thus, NOD/Lt T cells triggered by immunization to MT hsp65 in vivo or activated by Con A in vitro manifest an inherent response to human hsp65.

Human hsp65 is not itself a mitogen; adult mice of strains that do not spontaneously develop IDDM, such as C57BL/6, (Groups 5 and 6) or C57BL/KS (Groups 7 and 8), do not manifest T cell reactivity following Con A stimulation.

Finally, Table 9 illustrates that activation of the anti-human hsp65 T cell populations in vitro with Con A enabled the T cells to transfer acute diabetes to 1 month old, prediabetic NOD/Lt mice (Groups 2 and 4).

The association between T cell responsiveness to human hsp65 and diabetes is confirmed in Table 10. In the experiment which generated the data for Table 10, T cell lines were obtained by repeatedly stimulating the spleen cells with MT hsp65 (5 μ/ml) as described in Maron (supra). Clones were isolated by limiting dilution of the line cells. The T cell clones were tested for their ability to transfer acute diabetes essentially as described with respect to Table 9, except that 5×10⁶ Con A activated cells were transferred intraperitoneally. The proliferative responses of the clones to the antigens were measured as the SI, as described for Table 9. The cpm of control cultures were 4,500–6,500 cpm and the standard deviations from the mean cpm were always less than 10%.

TABLE 10

Diabetogenic T Cell Clones Recognize Human hsp65

| T Cell Clone | Transfer of Acute Diabetes (Incidence) | Proliferative Responses (SI) To Antigens | | |
|---|---|---|---|---|
| | | human hsp65 | MT-hsp65 | E. Coli control |
| 27 | 9/11 | 16.9 | 7.1 | 0.9 |
| C7 | 10/12 | 23.8 | 6.7 | 1.1 |
| C9 | 10/15 | 38.5 | 5.8 | 1.2 |
| 21 | 0/13 | 6.3 | 2.8 | 1.0 |

The clones were found to respond more vigorously to human hsp65 than to MT hsp65 or to E. coli control antigen. In addition, clones 27, C7 and C9 which responded strongly to human hsp65 were diabetogenic while clone 21 which responded relatively weakly to human hsp65 was not able to transfer diabetes. As cloned T cells express antigen receptors of only one specificity, it may be concluded that acute diabetes may be transferred to prediabetic NOD/Lt mice by T cells recognizing an epitope on human hsp65, an epitope cross-reactive to some degree with an epitope on MT hsp65.

EXAMPLE 14

Virulent T Cells Vaccinate Against Spontaneous IDDM

Groups of 5–7 prediabetic, two month old female NOD/Lt mice were primed or not by intraperitoneal immunization with 50 μg of antigen in oil. Spleen cells of the mice were or were not activated by incubation with antigens (5 μg/ml) or Con A (1.25 μg/ml) as described with respect to Table 9 in Example 13. The cells were then transferred (25×10⁶) intraperitoneally into groups of 1 month old, prediabetic mice. The mice were examined for acute diabetes (hyperglycemia; blood glucose>200 mg/dl) 3 weeks later in the manner described in Example 13. Spontaneous IDDM was assayed at 8 months of age by hyperglycemia and insulitis. The results of this experiment are shown in Table 11. The differences from the control (group 1) were significant *p<0.01 as indicated. The numbers represent the cumulative results of 2–3 experiments.

TABLE 11

Anti-hsp65 T Cells Induce Acute Transient Diabetes and Vaccinate Against Late Spontaneous IDDM
Preparation of T cell inoculum

| Group | Priming in vivo | Activator in vitro | Number of mice inoculated | Acute Diabetes % incidence | Spontaneous IDDM % incidence |
|---|---|---|---|---|---|
| 1 | None | None | 72 | 0 | 81 |
| 2 | None | MT hsp65 | 20 | 70* | 15* |
| 3 | None | Con A | 15 | 60* | 2* |
| 4 | BSA | BSA | 10 | 0 | 70 |
| 5 | MT hsp70 | MT hsp70 | 21 | 0 | 71 |
| 6 | MP hsp65 | MT hsp65 | 20 | 80* | 0* |

As expected, the untreated control mice (Group 1) were not hyperglycemic at 7 weeks of age and spontaneous IDDM was seen in 81% at 8 months of age. In contrast, acute diabetes (blood glucose above 200 mg/dl) was transferred using spleen cells of pre-diabetic mice provided that the spleen cells had been activated in vitro by MT hsp65 (Group 2) or by Con A (Group 3).

Spleen cells obtained from mice that had been primed in vivo with MT hsp65, BSA or MT hsp70 were administered after activation with the respective antigen in vitro. Acute diabetes was induced by the anti-MT hsp65 cells (Group 6) but not by the anti-BSA or anti-MT hsp70 cells (Groups 4 and 5). In contrast to the Con A and MT hsp65 activated cells which respond strongly to human hsp65 (Tables 8 and 9), proliferative assays of the BSA or the MT hsp70 reactive cells detected no reactivity to MT hsp65 or to human hsp65 (not shown). Thus, the transfer of acute diabetes was specific for cell populations containing T cells responsive to human hsp65.

Table 11 also shows that an episode of acute diabetes was followed by a significant decrease in the incidence of spontaneous IDDM developing at 8 months. Inoculation of mice with anti-BSA or anti MT hsp70 spleen cells neither induced acute diabetes nor prevented spontaneous IDDM (Groups 4 and 5).

The ability of acute, adoptively transferred diabetes to abort spontaneous IDDM was also seen in experiments done with the anti-hsp65 T cell clones described above (Table 9). Thirty-one mice were injected with virulent clones 27, C7 or C9 and all became acutely diabetic within 1–2 weeks. They all recovered spontaneously from hyperglycemia within 2 weeks, and only 2 of the 31 developed spontaneous IDDM at the age of 8 months. In contrast, 13 mice injected with avirulent clone 21 did not develop acute diabetes, and 6 of these mice became spontaneously diabetic by the age of 6 months (P<0.01).

Thus, diabetes produced by adoptive transfer of anti-human hsp65 T cells is transient. However, not only did the mice recover from acute diabetes, they acquired resistance to the development of late spontaneous IDDM. Hence, rather than accelerating the onset, or aggregating the severity of the natural IDDM, exposure of pre-diabetic mice to virulent T cells actually led to acquisition of resistance to the diabetic process.

EXAMPLE 15

Attenuated T Cells Vaccinate against Autoimmunity to Hsp65 and Abort IDDM

T cell vaccines were constructed from the spleen cells of 3 month old prediabetic NOD/Lt mice by activating the cells by incubation with Con A or with MT hsp65 as described with respect to Table 8 in Example 13, and then attenuating the activated cells with gamma irradiation (1500R) or with glutaraldehyde (0.3%, 15 minutes) as described in Lider et al, *Proc. Natl. Acad. Sci. U.S.A.*, 84, 4577 (1987). Groups of 15 or 25, five week old prediabetic NOD/Lt female mice were then left unvaccinated or were vaccinated by intraperitoneal inoculation with $10^7$ treated spleen cells. At the age of 6 months, 5 mice of each group were studied for the proliferative responses of their splenic T cells to human hsp65 shown as the stimulation index (SI). The control cpm without added antigen were 2.465±235 and 2.246±185 for unvaccinated and vaccinated mice respectively. The remaining mice were bled for determination of antibodies to human hsp65 in a standard solid phase radioimmunoassay (Schechter et al, *J. Biol. Chem.*, 259, 6411–6419, (1984)). To detect serum antibodies, the microtiter plates were coated by incubation (50 µg/ml), with hsp65 (for anti-hsps65), insulin (for anti-insulin) or guinea pig anti-insulin positive for the DM idiotype (for anti-idiotypic antibody). The presence of antibodies to these antigens was detected by incubating the coated wells with test mouse sera (diluted 1:50) and developing the test with $^{125}$I-labelled goat anti-mouse Ig (Amersham, U.K.; $10^5$ cpm per well). To detect hsp65 antigen (or an antigen cross-reactive therewith), the wells were incubated with 1.5 µl of test serum diluted 1:5 and then overlayed with rabbit anti-hsp65 Ig (diluted 1:100). Binding was measured using $^{125}$I-labelled goat anti-rabbit Ig (Amersham). The relative titer signifies the cpm of the binding to human hsp65 of serum diluted 1:100. The mean cpm of serum anti-human hsp65 antibody obtained from non-diabetic 1 month old NOD/Lt mice was 1.450±194 cpm. Sera of the mice were assayed for the presence of hsp65 or cross-reactive antigen using a solid phase radioimmunoassay as described above. The results are shown in Table 12. The vaccinated mice differed significantly from the non-vaccinated control mice by *p<0.01.

The results shown in Table 12 establish that otherwise virulent Con A or MT hsp65 activated T cells can be attenuated by treatment with gamma-irradiation (1,500R) or with glutaraldehyde (0.3%) and used to vaccinate against spontaneous IDDM. Similar to what has been shown in other experimental diseases, irradiated or glutaraldehyde treated autoimmune T cells were not virulent and did not produce acute diabetes (data not shown). Prevention of IDDM was associated with a marked reduction in the spontaneous T cell and antibody reactivity of the vaccinated mice to human hsp65.

As is described in previous examples, damage to islets in NOD/Lt mice is marked by the appearance in the serum of a protein recognized by anti-hsp65 antibodies. As this serum antigen possibly originates from injured beta cells, it was of interest to see whether T cell vaccination had any effect on its quantity. It can be seen (Table 12) that administration of a T cell vaccine reduced markedly the amount of hsp65 or cross-reactive antigen appearing in the serum at 6 months of age. This decrease was associated with lack of detectable insulitis on histologic examination (not shown).

Thus, virulent anti-human hsp65 T cells activated by MT hsp65 or Con A could be attenuated and used to vaccinate NOD/Lt mice against the development of spontaneous IDDM. The vaccinated state was marked by a decrease in the immunological signs of the IDDM process: anti-human hsp65 T cells and antibodies. At the same time, there was a decrease in the amount of hsp65 or serum antigen cross-reactive with hsp65, explainable by the cessation of insulitis.

EXAMPLE 16

T Cell Vaccination Produces Resistance to Acute Induced Diabetes

In Example 9, it was shown that acute diabetes marked by insulitis and hyperglycemia could be induced in pre-diabetic NOD/Lt mice by immunizing them with MT hsp65 in oil. It was also noted that this form of acute diabetes was transient and actually led to resistance to late, spontaneous IDDM. This experiment investigates the effects of immunization to human hsp65 and the influence of T cell vaccination on acute, induced diabetes.

Groups of 4 week old female NOD/Lt mice were or were not vaccinated with $10^7$ Con A activated, glutaraldehyde treated spleen cells as described with respect to Table 12 in Example 15. Two weeks later the mice were challenged with MT hsp65 or human hsp65 (50 µg in oil) to induce acute diabetes. The mice were then investigated for the development of spontaneous IDDM at the age of 8 months by

TABLE 12

T Cell Vaccination Controls T Cell and Antibody Reactivity to Human hsp65, Reduces Serum hsp65 Cross-Reactive Antigen and Aborts IDDM

| T cell vaccine | | Anti-Human-hsp65 immunity at 6 months | | | |
|---|---|---|---|---|---|
| Activation | Attenuation | T cell Antibody titer | | Serum hsp65 or cross-reactive antigen at 6 months | IDDM at 7 months |
| | | (SI) | (cpm × $10^{-3}$ ± SD) | (cpm × $10^{-3}$ ± SD) | (incidence) |
| None | None | 11.3 | 3.5 ± 0.7 | 3839 ± 688 | 16/20 |
| Con A | Irradiation | 2.5* | N.D. | N.D. | 1/10* |
| Con A | Glutaraldehyde | 2.7* | N.D. | 1930 ± 570* | 0/10* |
| MT hsp65 | Glutaraldehyde | 4.3* | 2.0 ± 0.4* | N.D. | 2/10* | measuring hyperglycemia and insulitis as described in Example 13. The results are shown in Table 13. Significant differences were *p<0.01.

TABLE 13

T Cell Vaccination Against Acute, hsp65 Induced Diabetes and Against Spontaneous IDDM Induced Diabetes

| T cell vaccination | antigen challenge | Incidence | Blood glucose (mg/dl) | Incidence of Spontaneous IDDM |
|---|---|---|---|---|
| None | None | 0/10 | 151 ± 19 | 8/10 |
| None | Human hsp65 | 12/15 | 258 ± 22* | 2/15* |
| None | MT hsp65 | 8/10 | 339 ± 116* | 0/10* |
| Yes | MT hsp65 | 0/20 | 140 ± 20 | 1/20* |

It can be seen that the non-vaccinated mice responded to human hsp65 or to MT hsp65 and developed acute, transient diabetes. This was followed by resistance to spontaneous IDDM. The T cell treated mice, in contrast, were resistant to antigen-induced acute diabetes. They were also protected against spontaneous IDDM. Thus, T cell vaccination effectively produces resistance both to acute diabetes induced by artificial immunization and to late, spontaneous IDDM.

EXAMPLE 17

Peptide Synthesis

It was surmised that the key epitope on the human hsp65 molecule was an amino acid sequence which shows partial, but not perfect, homology with the MT hsp65 sequence. As the latter works less well, the sequence of the corresponding epitope is presumably slightly different.

A series of peptides beginning at the carboxy terminus of the human hsp65 sequence were synthesized, choosing sequences that showed slight differences between the mycobacterial and human sequences. One such peptide has amino acid sequence 437–460 of the human hsp65 molecule shown in FIG. 3, i.e., H-Val-Leu-Gly-Gly-Gly-Cys-Ala-Leu-Leu-Arg-Cys-Ile-Pro-Ala-Leu-Asp-Ser-Leu-Thr-Pro-Ala-Asn-Glu-Asp-OH. This peptide has been designated p277.

Control peptide p278 overlaps the carboxy end of p277 by 3 amino acids and has the following sequence: H-Asn-Glu-Asp-Gln-Lys-Ile-Gly-Ile-Glu-Ile-Ile-Lys-Arg-Thr-Leu-Lys-Ile-OH. This corresponds to amino-acid sequence 458–474 of FIG. 3.

EXAMPLE 18

Immune Response to p277 in Diagnosis of Developing IDDM

Figure 5:
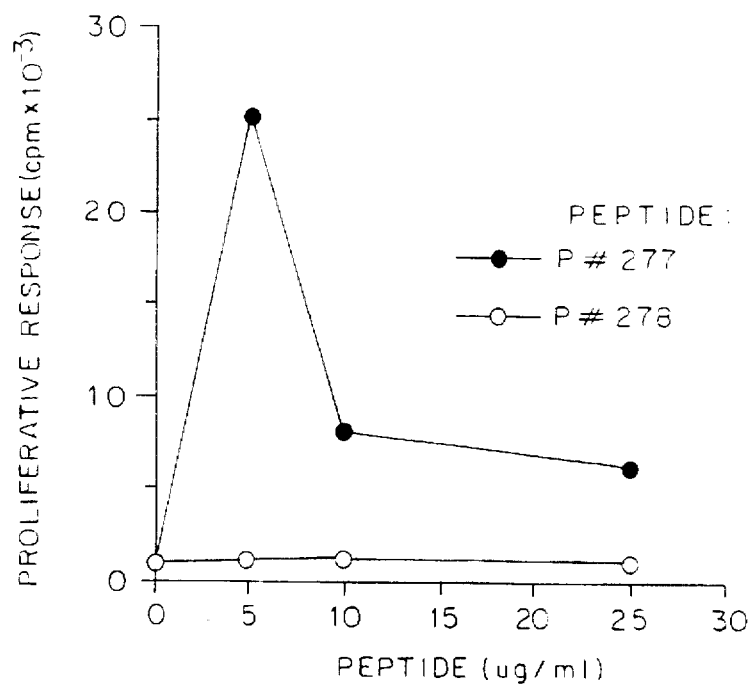
FIG. 5 is a graph showing the T cell proliferative response to p277 and p278 as a function of the concentration of peptide.

Suspensions of spleen cells from pre-diabetic 3 month old female NOD/Lt mice were tested for their proliferative responses to p277 in the manner described in Example 12 and the results are shown in FIG. 5. Although these mice will not develop overt IDDM for another 1–3 months, their spleen T cells show a strong response to p277 but not to p278. The optimal concentration of peptide in this and other in vitro experiments is 5 µg/ml.

EXAMPLE 19

Pathogenic T cell Clones Respond to p277 and to hsp65 Variants

Figure 6:
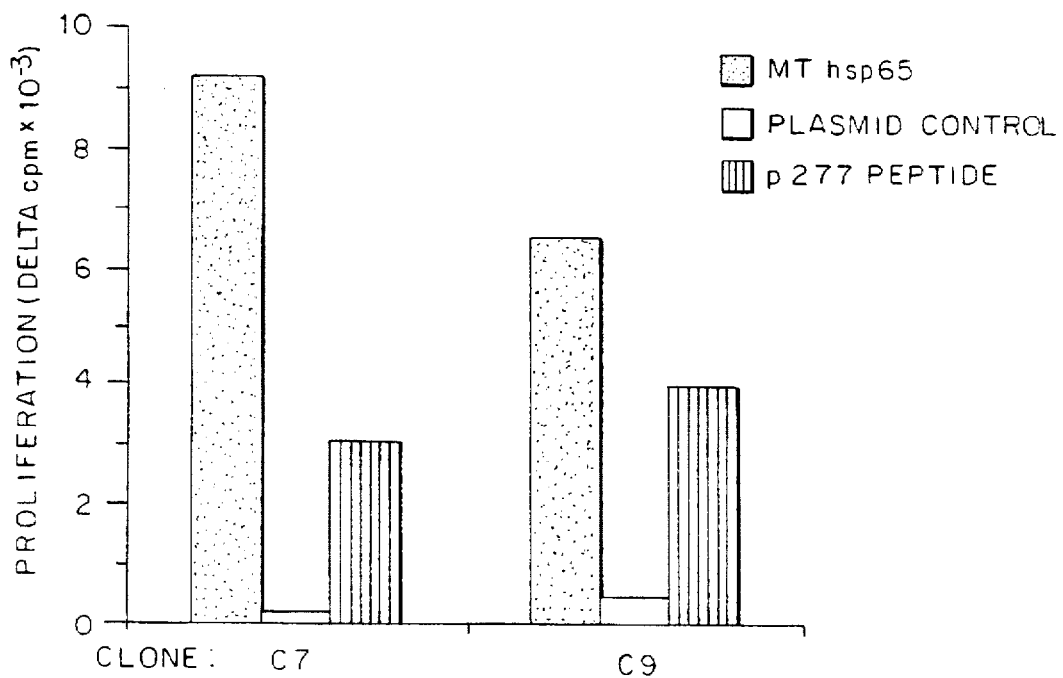
FIG. 6 is a bar graph showing the proliferation of C7 and C9 T cell clones, which are capable of transferring acute diabetes to young, prediabetic NOD/Lt mice, in response to p277, MT hsp65 and plasmid control.

FIG. 6 demonstrates that the C7 and C9 T cell clones, capable of transferring acute diabetes to young, prediabetic NOD/Lt mice (see Table 10, above), respond to p277. The clones are seen to respond to p277 as well as to the whole mycobacterial hsp65, but not to a control preparation of the plasmid not containing the hsp65 gene. Thus, it can be concluded that the p277 peptide contains a pathogenic epitope because pathogenic T cells recognize it.

The p277 epitope is also present in the mycobacterial hsp65 molecule because C7 and C9 also respond to that molecule. Hence, the mycobacterial hsp65 sequence which is homologous to the p277 sequence is immunologically functional. The mycobacterial sequence follows, with the substitution from the p277 human sequence underlined: H-Val-Ala-Gly-Gly-Gly-Val-Thr-Leu-Leu-Gln-Ala-Ala-Pro-Thr-Leu-Asp-Glu-Leu-Lys——Leu-Glu-Gly-Asp-OH. It can be seen that 13 of the 24 amino acids are substituted. Therefore, we can conclude that the immunological properties of the p277 peptide can tolerate about 60% changes in the sequence. Even if the minimal epitope were to be 10 amino acids rather than 24, there is no 10 amino acid sequence of p277 that does not differ by at least 4 to 6 amino acids from the mycobacterial sequence.

EXAMPLE 20

Peptide p277 Can be Used as Treatment Against Diabetes

It was demonstrated in Example 10 that the whole hsp65 molecule in non-immunogenic form can induce resistance in NOD/Lt mice to acute diabetes induced by immunization to immunogenic hsp65 in adjuvant. FIG. 7 shows that peptide p277, but not p278, could also be used to obtain resistance to induced diabetes. Groups of 7 five week old pre-diabetic NOD/Lt female mice were treated with 50 µg of p277 or p278 in incomplete Freund's adjuvant. Two weeks later, the mice were immunized with 50 µg of immunogenic hsp65 in incomplete Freund's adjuvant to induce acute diabetes. Three weeks later, blood glucose was measured. It can be seen that none of the mice treated with p277 became hyperglycemic (blood glucose of 200 mg/dl or greater). In contrast, 5 of the 7 mice treated with peptide p278 became diabetic.

The treatment with p277 also prevented the development of spontaneous diabetes in all 7 of these mice, while 80% of control mice that had been treated with a variety of antigens, such as bovine serum albumin or hsp70, went on to develop diabetes by 7 months of age. Thus, treatment with p277 led to resistance to both induced and spontaneous diabetes. Hence, a specific peptide can produce the therapeutic effect seen with the whole hsp65 molecule administered in non-immunogenic form.

Although the above data with p277 relate to the diabetes of NOD mice, it is obvious that the peptide, like the whole hsp65 molecule or any other molecule immunologically cross-reactive therewith, can be used for diagnosis or treatment in humans. This is because the diabetes of NOD mice is recognized as a faithful model of human IDDM. Moreover, it has been taught by Todd et al, *Nature*, 329:599, (1987) that NOD mice have a major histocompatibility complex (MHC) class II molecule (IA) similar to that of the human $DQ_\beta$ associated with human IDDM. It can then be expected that human and NOD diabetogenic T cells both should recognize the same peptide sequence presented by the MHC class II molecule lacking aspartic acid at position 57 of the $DQ_\beta$ chain. If humans and NOD mice developing diabetes see a similar peptide antigen, such as p277, then such peptide can be used in humans as well as in NOD mice for diagnosis and treatment of IDDM.

The particular protein produced by the human body during development of IDDM, which serves as a diagnostic marker in accordance with the present invention for the incipient outbreak of IDDM, is the human heat shock protein having a size of about 65 KD (or an antigen cross-reactive therewith). The nucleotide and deduced amino acid sequence of the 65 KD human heat shock protein are set forth in FIG. 3. This protein will hereinafter be referred to as hHSP65. Other proteins may also be produced in vivo which cross-react with the same antibodies which bind the 65 KD protein. For example, in mice and rats, 47 KD, 30 KD and 25 KD molecules were found which also cross-react with a monoclonal antibody specific to the hsp65 molecule of M. tuberculosis. A 47 KD molecule has also been discovered in rat fibroblasts which is cross-reactive with such an antibody. In view of the cross-species preservation of heat shock protein, it is fully expected that these will also be present in humans. Furthermore, the protein released into the blood and urine during development of IDDM may be a molecule other than hHSP65 but which is cross-reactive therewith. It may be a surface protein found on beta cells or even a fragment of a protein which retains an epitope which is present on hHSP65.

Accordingly, the molecule which serves as the diagnostic marker for the presence or incipience of IDDM, the presence of which in the blood or urine is being assayed in accordance with the present invention, is one which immunologically reacts with polyclonal antibodies raised against hHSP65, and, preferably, with monoclonal or polyclonal antibodies raised against the p277 sequence of hHSP65. For the purpose of the present specification and claims, the term "hHSP65" is intended to comprehend not only the 65 KD human heat shock protein, but also any other related molecule found in the human serum which cross-reacts with polyclonal antibodies raised against a 65 KD heat shock protein of any species. This definition is specifically intended to include, although it is not limited to, the 65 KD, 30 KD, 25 KD and 47 KD proteins which have already been discovered and are discussed herein.

Because of the structural similarities of heat shock proteins throughout nature, the presence of the diagnostic marker disclosed herein can be detected by polyclonal or monoclonal antibodies specifically raised against the heat shock protein of any organism. For example, the heat shock protein of M. tuberculosis (MT) can be readily produced in high quantity by genetic engineering techniques. This protein can be used to raise antibodies in rabbits or mice. The polyclonal rabbit anti-MT-hsp65 antibodies can be used in accordance with the present invention to assay for the presence of hHSP65. Similarly, monoclonal antibodies obtained from the spleens of mice immunized against MT hsp65 can be selected which react with MT hsp65. Such monoclonal antibodies will also cross-react with hHSP65. Preferred monoclonal antibodies are those raised against the p277 protein as this protein has been shown to contain a pathogenically active epitope.

Any specific monoclonal antibodies used in the examples of the present specification are for the purpose of exemplification only. There is no reason to believe that any one such monoclonal antibody specifically raised for its property of specifically reacting with a given antigen, would be better than any other for the purpose of the present invention.

As indicated above, not only can the hHSP65 protein (or a molecule cross-reactive therewith) be used as the diagnostic marker, but antibodies against hHSP65 can also be used as such. Antibodies which spontaneously form when hHSP65 or related protein is released in the human patient can be assayed. A positive assay for the presence of such antibodies will serve as an indication of impending IDDM to the same extent as an assay for the hHSP65 or related proteins themselves will serve this purpose. The anti-hHSP65 antibodies may be assayed for by looking for reaction with any hsp65 protein. Thus, the MT hsp65 protein will cross-react with anti-hHSP65 antibodies. Of course, the preferred protein for use in assaying for the presence of anti-hHSP65 antibodies is the hHSP65 protein, and, more preferably, the p277 sequence thereof. However, those of ordinary skill in the art can readily empirically determine, without undue experimentation, whether any given protein or protein fragment will cross-react with anti-hHSP65 antibodies. Simple in vitro tests can be used to determine if any such protein or other molecule will immunoreact with anti-hHSP65 antibodies. If it does, then it can be used in the method of the present invention and it is intended to be comprehended by the present invention.

While the p277 sequence has been shown to correspond to a pathogenic epitope in NOD/Lt mice in the experiments detailed above, in another strain of mouse, C57BL/6, in which diabetes can be induced by human hsp65 and whose T cells respond to human hsp65, the T cells do not respond to p277. Thus, it is evident that this is not the only pathogenic epitope on hHSP65. Indeed, the diagnostic marker protein found in the blood and urine of pre-diabetic human patients has been characterized as having a molecular weight of about 62 KD. Accordingly, it would be expected that the particular epitope (human leukocyte antigen, HLA) presented by the major histocompatibility complex (MHC) may differ from individual to individual. Thus, while the p277 sequence is presently preferred, those of ordinary skill in this art will understand that other antigenic sequences in the hHSP65 protein will also be found to have the same or related effect as p277. The present invention is intended to cover all such sequences.

The above examples show that not only can the hsp65 protein or cross-reactive antigen and antibodies specific thereto be used as the diagnostic maker for incipient diabetes, but also T cells which are specific to such proteins. Indeed, it appears that the appearance of such specific T cells may preceed the appearance of antibodies. It is the T cells which actually attack the beta cells, rather than the antibodies. Those of ordinary skill in the art will be aware of many assays for T cell activity against a particular antigen. For example, peripheral lymphocytes can be obtained from a test subject, subjected to hHSP65 or a cross-reactive antigen, and any of various known effects which occur upon activation can be measured, such as proliferation, cytokine or lymphokine production, enzyme production, calcium flux, etc. Any such assay is within the skill of the art.

As noted above, hsp65 is known to be associated with adjuvant arthritis in rats and with rheumatoid arthritis in humans. There would be no uncertainty regarding the assay of hsp65 or anti-hsp65 in discriminating between persons developing IDDM and those suffering from arthritis because, unlike the IDDM process, the process of arthritis is manifested clearly by blatant signs and symptoms of arthritis. Hence, detection of hsp65 or anti-hsp65 without signs or symptoms of arthritis would serve to call attention to the possibility of subclinical beta cell destruction and incipient IDDM. Additional tests such as antibodies to beta cells could then be used to confirm a diagnosis of autoimmunity to beta cells.

The association of hsp90 with systemic lupus erythematosus (SLE) would also not be confused with the IDDM process because SLE is also characterized by clear signs and symptoms of illness, while the IDDM process is clinically silent.

Antibodies against hsp65 or related protein can be used for the diagnosis of IDDM in which hsp65 or another immunologically cross-reactive molecule is injected subcutaneously into a patient, and the occurrence of a detectable skin reaction is observed. Alternatively, hsp65 or related molecule may be contacted with a patient's blood or blood component, and the occurrence of any immunological reaction with anti-hHSP65, i.e., any antibody which cross-reacts with hsp65, present in the patient's blood, detected by any known immunological method. Such well known immunological methods include radioimmunoassay, fluorescent immunoassay, ELISA, chemiluminescent assay, and the like.

In the in vivo skin test, the skin reaction at the site of the injection is measured after a sufficient time period, for example, 24 to 72 hours after administration. Swelling and/or redness is due to a delayed hypersensitivity-like reaction.

For the in vitro serological tests, serum of a patient is contacted with hsp65 or related molecule. If the serum contains antibodies against antigenic determinants of hsp65, an immunological reaction will occur which may be detected and assayed by means of standard techniques such as ELISA, agglutination, etc.

Any well known immunoassay technique can be used to detect the presence of hHSP65, anti-hHSP65 or hHSP65 specific T cells. It should be understood that once one of ordinary skill in the art becomes aware of the fact that the presence of anti-hHSP65 antibodies in the serum of a person, determined, for example, by means of assay with hsp65, is a positive indication of incipient or existing IDDM, such artisans would be well aware of the types of immunoassay technique which can be used. Besides radioimmunoassay (solid or liquid phase), any conventional immunoassay technique can be used, such as enzyme-linked immunosorbent assay (ELISA), heterogeneous immunoassay (both competitive and non-competitive) using labels other than enzymes and radioisotopes, homogeneous immunoassays based on fluorescence quenching and enzyme channeling, immune precipitation (including radial immune diffusion) and agglutination assays based on visual semi-quantitative detection or quantitative turbidimetric detection. The assay may use any conventional solid phase or sandwich assay techniques.

Similarly, kits may be prepared for carrying out any of the various assays used for accomplishing the present invention. Each such kit would include all of the materials necessary to conduct a single assay or a fixed number of assays. For example, such a kit for determining the presence of anti-hHSP65 antibodies may contain solid-phase immobilized hsp65 and a tagged antibody capable of recognizing the non-variable region of the anti-hHSP65 antibody to be detected, such as tagged anti-human Fab. A kit for determining the presence of hHSP65 may contain solid-phase immobilized antibody which reacts or cross-reacts with hHSP65, and a tagged antibody capable of reacting with a different epitope of hHSP65 than that recognized by the immobilized antibody. The kit should also contain reagent capable of precipitating immune complexes of hsp65 and anti-hHSP65 antibodies and may contain directions for using the kit and containers to hold the materials of the kit. Any conventional tag or label may be used, such as a radioisotope, an enzyme, a chromophore or a fluorophore. A typical radioisotope is iodine-125 or sulfur-35. Typical enzymes for this purpose include horseradish peroxidase, α-galactosidase and alkaline phosphatase.

Diagnostic compositions according to the present invention are prepared by combining hsp65 with suitable adjuvants and auxiliary components.

As shown from the above experiments, islet cells and heat shocked fibroblasts release molecules cross-reactive with mycobacterial hsp65. The fact that immunization of mycobacterial hsp65 can cause IDDM indicates that an immune attack against antigens cross-reactive with mycobacterial hsp65 damages beta cells. Such an immune response could occur as a primary event following accidental immunization to a cross-reactive hHSP65 or an invading microbe. The release of hHSP65 or related protein could also arise subsequent to beta cell damage inflicted by a virus or toxins. Thus, it can be understood why the appearance of the hsp65 positive molecules in the blood and urine is an early sign of developing IDDM, because the molecules are released from the beta cells as damage proceeds. Similarly, anti-hHSP65 antibodies are a reliable sign of impending IDDM because an immune response to hHSP65 can itself cause IDDM.

Whether the antibodies to hHSP65 are originally raised following accidental immunization or following release of hHSP65 subsequent to beta cell damage inflicted by a virus or toxins, production of anti-hHSP65 antibodies or anti-hHSP65 T-cells could enhance and perpetuate the process of beta cell destruction as the hHSP65 contained on the beta cells themselves will be attacked.

It is significant that spontaneous IDDM is averted following recovery from a bout of acute diabetes, either transferred by virulent anti-hsp65 T cells or induced by active immunization to hsp65. This suggests that the kinetics and magnitude of an autoimmune response can lead to its own regulation. Apparently an insidious, chronic process can "sneak through" the natural defenses to autoimmune disease, while an overt autoimmune stimulus may strengthen regulation. The acquisition of resistance to an autoimmune disease by an acute episode of the disease itself is seen regularly in the rat model of experimental autoimmune encephalomyelitis (EAE). Following spontaneous recovery from acute EAE induced either by active immunization to myelin basic protein or by passive transfer of activated T cells, rats manifest resistance to further attempts to induce EAE. It was found that an episode of EAE activated mechanisms, possibly anti-idiotypic suppression, capable of controlling the virulent T cells responsive to myelin basic protein.

T cell vaccination using attenuated autoimmune T cells appears to be a way of activating regulatory mechanisms without paying the price of acute disease. Anti-idiotypic and anti-ergotypic T cells of the kinds demonstrated in T cell vaccination against EAE quell the autoimmune anti-hsp65 T cells and so prevent the clinical emergence of IDDM.

This reasoning helps to explain how induction of tolerance or suppression of an immune response to hHSP65 prevents or cures the diabetic process even after it is initiated. Thus, hsp65, low molecular weight molecules (25, 30 or 47 KD) cross-reactive with hsp65, or fragments, modified peptide sequences, synthetic peptides or even organic molecules based on the fusion-protein blueprint and designed so as to satisfy the physico-chemical requirements of hsp65, can be used to prevent or treat the IDDM process, as long as they are cross-reactive with polyclonal antibodies raised against hHSP65 or they raise antibodies which are cross-reactive with hHSP65. The p277 sequence of hHSP65 is a preferred substance for this purpose. Furthermore, attentuated T cells specific to hHSP65 or related antigen can be used to induce such immunity or suppress such immune response, as can fragments or active portions thereof.

The hsp65 molecule has been shown to be useful as a therapeutic composition which is effective against continued development of IDDM by creating tolerance to hHSP65 and thus stopping the self-destruction of the beta cells. The active principle for use in such treatment of incipient IDDM can be any material which is immunologically cross-reactive with hHSP65, i.e., it either cross-reacts with polyclonal antibodies raised against hHSP65 or it raises antibodies which cross-react with hHSP65. Such material, be it a peptide, protein, carbohydrate or other substance, if administered in a tolerogenic manner, will serve to induce tolerance to hHSP65 by virtue of this cross-reactivity. If the substance is an hsp65 protein, it can come from any species. The substance need not be an entire protein in order to be immunologically cross-reactive with hHSP65. It could be a fragment of the protein which retains the antigenic activity of the protein itself, such as the p277 sequence. Routine experimentation will determine whether any given substance is cross-reactive with hHSP65. If the substance cross-reacts with a polyclonal antibody raised against hHSP65 or if it raises antibodies which are cross-reactive with hHSP65, then it is intended to be within the scope of the present invention insofar as therapy of incipient IDDM is concerned. Additional verification of the capability of such a substance to be operable in human therapy would be by means of testing for induction of tolerance in the mouse test described in Example 10. Such experimentation would be routine and would not involve undue experimentation.

The preferred compound for treatment of human IDDM is hHSP65. The amino acid sequence of a human heat shock protein is set forth in FIG. 3. This protein may be used for this purpose. The p277 sequence thereof is another particularly preferred molecule for this purpose.

Besides the hsp65 protein discussed herein, salts, functional derivatives, precursors and active fractions thereof having the ability to immunologically cross-react with hHSP65 may also be used. Sequences such as those of FIG. 3 or those disclosed in Van Eden et al, supra, in which one or more amino acids are deleted, added, or replaced with other amino acids, are intended to be encompassed by the present invention as long as they have the ability to immunologically cross-react with hHSP65.

As used herein the term "salts" refers to both salts of carboxyl groups and to acid addition salts of amino groups of the protein molecule. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid.

"Functional derivatives" as used herein covers derivatives which may be prepared from the functional groups which occur as side chains on the residues or the N- or C- terminal groups, by means known in the art, and are included in the invention as long as they remain pharmaceutically acceptable, i.e., they do not destroy the activity of the protein, do not confer toxic properties on compositions containing it and do not adversely affect the antigenic properties thereof.

These derivatives may, for example, include aliphatic esters of the carboxyl groups, amides of the carboxyl groups by reaction with ammonia or with primary or secondary amines, N-acyl derivatives of free amino groups of the amino acid residues formed with acyl moieties (e.g., alkanoyl or carbocyclic aroyl groups) or O-acyl derivatives of free hydroxyl group (for example that of seryl or threonyl residues) formed with acyl moieties. "Precursors" are compounds formed prior to, and converted into, hsp65 in the animal or human body.

As "active fractions" of the substantially purified protein, the present invention covers any fragment or precursors of the polypeptide chain of an hsp65 protein molecule alone or together with associated molecules or residues linked thereto, e.g., sugar or phosphate residues, or aggregates of the protein molecule or the sugar residues by themselves, provided said fraction has the ability to immunologically cross-react with hHSP65. One example of such an active fraction is the p277 sequence of hHSP65.

It is critical that the active principle described above be administered in a manner which will induce tolerance rather than inducing an immunogenic response. Thus, it should not be administered in oil or any other immunogenic adjuvant. A preferred way of administering the active principle such that it will induce tolerance is to administer it with a carrier that favors induction of tolerance to the antigen when the antigen-carrier conjugate is administered. Such carriers are known as tolerogenic carriers. Examples of known tolerogenic carriers are polymers of D-amino acids, polyethylene glycol, polymers of sugar molecules, self-IgG molecules, self-spleen cells, and fatty acid molecules. An antigen may also be administered in a monomeric highly soluble form to induce tolerance. Another known method of inducing tolerance to an antigen is to administer it orally, even without any carrier specifically chosen for its tolerogenic characteristics. Particular manners of administering an antigen so as to induce tolerance are known to those of ordinary skill in the art and any such manner may be used in accordance with the present invention. Such techniques are not, per se, part of the present invention.

The T cell preparations which may be used for prevention or treatment of IDDM are obtained from T cells which have developed specificity for the IDDM specific antigens discussed above, i.e., specific to hHSP65 or an antigen cross-reactive therewith, such as p277. These specific cells must also have been activated either by incubating in the presence of such antigen or by incubating with a mitogen capable of inducing an immune response by the T cells, such as concanavalin A. Such activated IDDM specific T cells are preferably attentuated, such as by irradiation. A preferred means of attenuation, which also has the salutary effect of increasing the immunogenicity of the T cells, is by pressure treatment by means of hydrostatic pressure of sufficient pressure and time to cause augmented immunogenicity of the T cells without substantial loss of membrane protein therefrom. Alternatively, the pressure may be of sufficient magnitude and duration to cause the cell surface proteins to be shed from the cells. After low speed centrifugation to remove the cells, the fragments obtained after high speed centrifugation may be used as the vaccine, as well as the soluble proteins remaining in the supernatant after high speed centrifugation. All of these techniques are described in detail in European patent publication 261,648 of the present assignee, the entire contents of which are hereby incorporated by reference.

The IDDM specific, activated T cells may also be treated with a chemical cross-linking agent, such as formaldehyde, glutaraldehyde or a photoactivatable psoralen cross-linking agent such as 8-methoxypsoralen (see European patent publication 333,606 to the present assignee, the entire contents of which are hereby incorporated by reference). Such T cells may also be treated with a cytoskeletal disrupting agent, such as cytochalsin or colchicine. Any one or more of the pressure-treatment, chemical cross-linker treatment and cytoskeletal disrupting agent treatment steps can be combined. In addition, the cells so treated may be lysed and only the fixed cell membranes recovered and used. All of these processes are described in detail in European patent publication 261,648.

The variable region of the T cell receptor specific to the IDDM antigen, i.e., hHSP65 or an antigen cross-reactive therewith, and preferably the VDJ region thereof, may be isolated and, preferably, cloned for expression, and used as the T cell vaccine preparation of the present invention in the manner discussed in Howell, supra, and Vandenbark, supra, for the autoimmune encephalomyelitis T cell receptor.

Once the IDDM antigen is known, as is disclosed herein, all of these known techniques may be applied for the first time with respect to IDDM. All of such techniques can be accomplished by those of ordinary skill in this art without undue experimentation once the antigen is known. Accordingly, the present invention is intended to comprehend all such techniques. All of these represent additional methods of using the antigen of the present invention.

Such a tolerogenic composition may be administered as a vaccine for the prevention of the development of IDDM, for example in family members of IDDM patients who may be genetically at risk for the development of IDDM. Preferably, however, the composition is used to stop the continued development of IDDM in persons having detectable hHSP65 in the blood or urine but preferably before they have developed an immune response to the hHSP65. Induction of tolerance will prevent that immune response and therefore prevent the damage (IDDM) caused by an uncontrolled anti-hHSP65 response. However, it is not too late to use the composition of the present invention as treatment even after the appearance of anti-hHSP65 antibodies. The experiments the results of which are shown in Tables 8 and 13 establish that the present invention can serve to stop the immune response even after autoimmunity to the islets has already begun. As the autoimmune process may take years in humans, even down-regulation of the response would be beneficial.

The hsp65 or related molecule (as discussed above) can be used as immunogen in pharmaceutical compositions, particularly vaccines for the alleviation and treatment of IDDM, as well as antigens in diagnostic compositions for the diagnosis of IDDM. These pharmaceutical and diagnostic compositions, which may be prepared in a manner known in the art, also form part of the present invention.

Another way to improve the efficacy as a vaccine or therapeutic agent of the hsp65 is to construct, by known genetic engineering methods, microorganisms expressing the hsp65 either as such or as part of a fusion protein or as a multimer thereof. These microorganisms themselves can be used for the preparation of a live vaccine which will provoke not only the production of antibodies against the micro-organism in question, but will also be useful for the alleviation and treatment of IDDM. These genetically engineered microorganisms, and pharmaceutical compositions containing these, are also part of the present invention. Examples of suitable genetically engineered microorganisms are Vaccinia and Salmonella strains.

The composition in accordance with the present invention may be administered orally or parenterally, such as subcutaneously, intramuscularly, intravenously, intranasally or intrarectally. The pharmaceutical tolerogenic compositions may be prepared in a manner known in the art.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A substantially pure polypeptide which is capable of down-regulating the autoimmune response causing destruction of insulin-producing beta cells when administered to a patient undergoing autoimmune destruction of the insulin-producing beta cells, comprising the 24 amino acid sequence Val-Leu-Gly-Gly-Gly-Cys-Ala-Leu-Leu-Arg-Cys-Ile-Pro-Ala-Leu-Asp-Ser-Leu-Thr-Pro-Ala-Asn-Glu-Asp, but which is not an entire heat shock protein.

2. A polypeptide in accordance with claim 1, consisting of said 24 amino acid sequence.

3. A substantially pure polypeptide which is capable of down regulating the autoimmune response causing destruction of insulin-producing beta cells when administered to a patient undergoing autoimmune destruction of the insulin-producing beta cells, comprising the 23 amino acid sequence Val-Ala-Gly-Gly-Gly-Val-Thr-Leu-Leu-Gln-Ala-Ala-Pro-Thr-Leu-Asp-Glu-Leu-Lys-Leu-Glu-Gly-Asp, but which is not an entire heat shock protein.

4. A polypeptide in accordance with claim 3, consisting of said 23 amino acid sequence.

5. A pharmaceutical composition for down-regulating the autoimmune response causing destruction of insulin-producing beta cells, comprising a pharmaceutically acceptable tolerogenic carrier conjugated to an active principle selected from the group consisting of:

a) the 65 KD human heat shock protein;
   b) *Mycobacterium tuberculosis* hsp65; and
   c) a polypeptide comprising the amino acid sequence Val-Leu-Gly-Gly-Gly-Cys-Ala-Leu-Leu-Arg-Cys-Ile-Pro-Ala-Leu-Asp-Ser-Leu-Thr-Pro-Ala-Asn-Glu-Asp, or a variant thereof wherein one or more of the underlined substitutions or deletion in the following sequence has been made: Val-Ala-Gly-Gly-Gly-Val-Thr-Leu-Leu-Gln-Ala-Ala-Pro-Thr-Leu-Asp-Glu-Leu-Lys——Leu-Glu-Gly-Asp.

6. A composition in accordance with claim 5, wherein said active principle is a polypeptide comprising the amino acid sequence Val-Leu-Gly-Gly-Gly-Cys-Ala-Leu-Leu-Arg-Cys-Ile-Pro-Ala-Leu-Asp-Ser-Leu-Thr-Pro-Ala-Asn-Glu-Asp, or a variant thereof wherein one or more of the underlined substitutions or deletion in the following sequence has been made: Val-Ala-Gly-Gly-Gly-Val-Thr-Leu-Leu-Gln-Ala-Ala-Pro-Thr-Leu-Asp-Glu-Leu-Lys——Leu-Glu-Gly-Asp.

7. A composition in accordance with claim 5, wherein said active principle is the 65 KD human heat shock protein.

8. A composition in accordance with claim 5, wherein said active principle is *Mycobacterium tuberculosis* hsp65.

9. A composition in accordance with claim 6, wherein said polypeptide comprises the 24 amino acid sequence Val-Leu-Gly-Gly-Gly-Cys-Ala-Leu-Leu-Arg-Cys-Ile-Pro-Ala-Leu-Asp-Ser-Leu-Thr-Pro-Ala-Asn-Glu-Asp.

10. A composition in accordance with claim 9 wherein said polypeptide consists of said 24 amino acid sequence.

11. A composition in accordance with claim 9 wherein said polypeptide is a fragment of the human 65 kD heat shock protein.

12. A method for down-regulating the autoimmune response causing destruction of insulin-producing beta cells in a patient undergoing autoimmune destruction of the insulin-producing beta cells, comprising administering to such patient, in a manner which suppresses a diabetogenic immune response to the 65 KD human heat shock protein, an active principle selected from the group consisting of:

a) the 65 KD human heat shock protein;

b) *Mycobacterium tuberculosis* hsp65; and c) a polypeptide comprising the amino acid sequence Val-Leu-Gly-Gly-Gly-Cys-Ala-Leu-Leu-Arg-Cys-Ile-Pro-Ala-Leu-Asp-Ser-Leu-Thr-Pro-Ala-Asn-Glu-Asp, or a variant thereof wherein one or more of the underlined substitutions or deletion in the following sequence has been made: Val-Ala-Gly-Gly-Gly-Val-Thr-Leu-Leu-Gln-Ala-Ala-Pro-Thr-Leu-Asp-Glu-Leu-Lys——Leu-Glu-Gly-Asp.

13. A method in accordance with claim 12 wherein said active principle is a polypeptide comprising the amino acid sequence Val-Leu-Gly-Gly-Gly-Cys-Ala-Leu-Leu-Arg-Cys-Ile-Pro-Ala-Leu-Asp-Ser-Leu-Thr-Pro-Ala-Asn-Glu-Asp, or a variant thereof wherein one or more of the underlined substitutions or deletion in the following sequence has been made: Val-Ala-Gly-Gly-Gly-Val-Thr-Leu-Leu-Gln-Ala-Ala-Pro-Thr-Leu-Asp-Glu-Leu-Lys——Leu-Glu-Gly-Asp.

14. A method in accordance with claim 12 wherein said active principle is the 65 KD human heat shock protein.

15. A method in accordance with claim 12 wherein said active principle is *Mycobacterium tuberculosis* hsp65.

16. A method in accordance with claim 13 wherein said polypeptide comprises the 24 amino acid sequence Val-Leu-Gly-Gly-Gly-Cys-Ala-Leu-Leu-Arg-Cys-Ile-Pro-Ala-Leu-Asp-Ser-Leu-Thr-Pro-Ala-Asn-Glu-Asp.

17. A method in accordance with claim 16 wherein said polypeptide consists of said 24 amino acid sequence.

18. A method in accordance with claim 16 wherein said polypeptide is a fragment of the human 65 kD heat shock protein.

* * * * *

UNITED STATES PATENT AND TRADEMARK OFFICE
CERTIFICATE OF CORRECTION

PATENT NO. : 5,780,034

DATED : July 14, 1998

INVENTOR(S) : Irun R. Cohen; Dana Elias; Doron Markovits

It is certified that error appears in the above-identified patent and that said Letters Patent is hereby corrected as shown below:

Column 6, line 2, change "5 μm/well" to --5 μg/well--.
Column 20, lines 13-14, change "H-Val-Ala-Gly-Gly-Gly-Val-Thr-Leu-Leu-Gln-Ala-Ala-Pro-Thr-Leu-Asp-Glu-Leu-Lys- — -Leu-Glu-Gly-Asp-OH" to --H-Val-<u>Ala</u>-Gly-Gly-Gly-<u>Val</u>-<u>Thr</u>-Leu-Leu-<u>Gln</u>-<u>Ala</u>-<u>Ala</u>-Pro-<u>Thr</u>-Leu-Asp-<u>Glu</u>-Leu-<u>Lys</u>- — -<u>Leu</u>-<u>Glu</u>-Gly-Asp-OH--.
Column 28, lines 43-45 (claim 5, lines 13-15), change "Val-Ala-Gly-Gly-Gly-Val-Thr-Leu-Leu-Gln-Ala-Ala-Pro-Thr-Leu-Asp-Glu-Leu-Lys- — -Leu-Glu-Gly-Asp" to --Val-<u>Ala</u>-Gly-Gly-Gly-<u>Val</u>-<u>Thr</u>-Leu-Leu-<u>Gln</u>-<u>Ala</u>-<u>Ala</u>-Pro-<u>Thr</u>-Leu-Asp-<u>Glu</u>-Leu-<u>Lys</u>- — -Leu-<u>Glu</u>-Gly-Asp--.
Column 28, lines 52-54 (claim 6, lines 7-9), change "Val-Ala-Gly-Gly-Gly-Val-Thr-Leu-Leu-Gln-Ala-Ala-Pro-Thr-Leu-Asp-Glu-Leu-Lys- — -Leu-Glu-Gly-Asp" to --Val-<u>Ala</u>-Gly-Gly-Gly-<u>Val</u>-<u>Thr</u>-Leu-Leu-<u>Gln</u>-<u>Ala</u>-<u>Ala</u>-Pro-<u>Thr</u>-Leu-Asp-<u>Glu</u>-Leu-<u>Lys</u>- — -Leu-Glu-Gly-Asp--.

UNITED STATES PATENT AND TRADEMARK OFFICE
CERTIFICATE OF CORRECTION

PATENT NO. : 5,780,034
DATED : July 14, 1998
INVENTOR(S) : Irun R. Cohen; Dana Elias, Doron Markovits It is certified that error appears in the above-identified patent and that said Letters Patent is hereby corrected as shown below:

Column 29, lines 15-17 (claim 12, lines 15-17), change
"Val-Ala-Gly-Gly-Gly-Val-Thr-Leu-Leu-Gln-Ala-Ala-Pro-
Thr-Leu-Asp-Glu-Leu-Lys- — -Leu-Glu-Gly-Asp" to
--Val-<u>Ala</u>-Gly-Gly-Gly-<u>Val</u>-<u>Thr</u>-Leu-Leu-<u>Gln</u>-<u>Ala</u>-<u>Ala</u>-Pro-
<u>Thr</u>-Leu-Asp-<u>Glu</u>-Leu-<u>Lys</u>-<u>—</u>-<u>Leu</u>-<u>Glu</u>-Gly-Asp--.
Column 30, lines 4-6 (claim 13, lines 7-9), change
"Val-Ala-Gly-Gly-Gly-Val-Thr-Leu-Leu-Gln-Ala-Ala-Pro-
Thr-Leu-Asp-Glu-Leu-Lys- — -Leu-Glu-Gly-Asp" to
--Val-<u>Ala</u>-Gly-Gly-Gly-<u>Val</u>-<u>Thr</u>-Leu-Leu-<u>Gln</u>-<u>Ala</u>-<u>Ala</u>-Pro-
<u>Thr</u>-Leu-Asp-<u>Glu</u>-Leu-<u>Lys</u>-<u>—</u>-<u>Leu</u>-<u>Glu</u>-Gly-Asp--.

Signed and Sealed this

Seventh Day of December, 1999

Attest:

Q. TODD DICKINSON

Attesting Officer

Acting Commissioner of Patents and Trademarks